United States Patent
Batta et al.

(10) Patent No.: US 11,918,382 B2
(45) Date of Patent: Mar. 5, 2024

(54) CONTINUAL BACKGROUND MONITORING OF EYE HEALTH

(71) Applicant: International Business Machines Corporation, Armonk, NY (US)

(72) Inventors: Raghav Batta, Danbury, CT (US); Elnatan Mataev, Poughkeepsie, NY (US); Heidi E. Fritz, Raleigh, NC (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 750 days.

(21) Appl. No.: 16/847,137

(22) Filed: Apr. 13, 2020

(65) Prior Publication Data

US 2021/0315499 A1   Oct. 14, 2021

(51) Int. Cl.
*A61B 5/00* (2006.01)
*A61B 3/00* (2006.01)
(Continued)

(52) U.S. Cl.
CPC .......... *A61B 5/6898* (2013.01); *A61B 3/0025* (2013.01); *A61B 3/113* (2013.01);
(Continued)

(58) Field of Classification Search
CPC .. A61B 3/113; A61B 3/10; A61B 3/11; A61B 3/14; A61B 3/145; A61B 3/028;
(Continued)

(56) References Cited

U.S. PATENT DOCUMENTS

| 5,880,702 A | 3/1999 | Morimoto et al. |
| 6,238,049 B1 | 5/2001 | Griffin et al. |

(Continued)

FOREIGN PATENT DOCUMENTS

| CN | 107124607 A | 9/2017 |
| CN | 107659598 A | 2/2018 |

(Continued)

OTHER PUBLICATIONS

Machine translation of KR 20190034136 A (Year: 2022).*

(Continued)

*Primary Examiner* — David J. McCrosky
(74) *Attorney, Agent, or Firm* — Amin, Turocy & Watson, LLP

(57) ABSTRACT

Systems and techniques that facilitate background monitoring of eye health are provided. In various embodiments, a system can comprise a sensor component of a device. In various aspects, the sensor component can detect one or more physical characteristics associated with an entity. In various embodiments, the system can further comprise a diagnostic component of the device. In various instances, the diagnostic component can estimate in a background of the device a health condition of an eye of the entity based on the one or more physical characteristics. In various cases, estimating the health condition in the background of the device can facilitate real-time monitoring of the eye health of the entity without interrupting the entity's normal use of the device.

20 Claims, 16 Drawing Sheets

(51) Int. Cl.
*A61B 3/113* (2006.01)
*A61B 3/14* (2006.01)
*G06T 7/00* (2017.01)
*G16H 50/20* (2018.01)
*G16H 50/30* (2018.01)
*A61B 3/10* (2006.01)

(52) U.S. Cl.
CPC .............. *A61B 3/14* (2013.01); *A61B 5/0035* (2013.01); *A61B 5/004* (2013.01); *A61B 5/746* (2013.01); *G06T 7/0012* (2013.01); *G16H 50/20* (2018.01); *G16H 50/30* (2018.01); *A61B 3/101* (2013.01); *A61B 3/145* (2013.01); *A61B 5/4863* (2013.01); *A61B 5/7264* (2013.01); *G06T 2207/30041* (2013.01)

(58) Field of Classification Search
CPC ....... A61B 3/032; A61B 3/112; A61B 3/0025; A61B 3/0033; A61B 3/0041; A61B 3/005; A61B 3/08; A61B 3/101; A61B 3/103; A61B 5/6898; A61B 5/746; A61B 5/4863; G16H 50/20; G16H 50/30
See application file for complete search history.

(56) References Cited

U.S. PATENT DOCUMENTS

| | | |
|---|---|---|
| 7,350,921 B2 | 4/2008 | Ridings |
| 7,367,675 B2 | 5/2008 | Maddalena et al. |
| 7,575,321 B2 * | 8/2009 | Newman ................ G16H 50/20 351/205 |
| 8,911,087 B2 | 12/2014 | Publicover et al. |
| 9,230,062 B2 * | 1/2016 | Seriani ................ A61B 3/0033 |
| 9,241,620 B1 * | 1/2016 | Kockan ................ A61B 3/0025 |
| 9,579,060 B1 * | 2/2017 | Lisy ........................ A61B 5/16 |
| 9,980,644 B2 * | 5/2018 | Fried ....................... G16H 10/60 |
| 10,248,197 B2 * | 4/2019 | Abed Aljawad .... G06F 3/04842 |
| 11,051,689 B2 * | 7/2021 | Antony ................ A61B 3/113 |
| 11,141,107 B2 * | 10/2021 | Arnold ................... A61B 5/112 |
| 2004/0105073 A1 | 6/2004 | Maddalena et al. |
| 2006/0078858 A1 | 4/2006 | Vroman et al. |
| 2008/0040719 A1 | 2/2008 | Shimizu et al. |
| 2013/0141697 A1 | 6/2013 | Berry et al. |
| 2014/0028973 A1 | 1/2014 | Scolaro |
| 2017/0156585 A1 | 6/2017 | Nie et al. |
| 2017/0181825 A1 | 6/2017 | Hunter |
| 2017/0311793 A1 | 11/2017 | Green |
| 2017/0323485 A1 | 11/2017 | Samec et al. |
| 2018/0160981 A1 * | 6/2018 | Tsymbalenko ....... A61B 8/5215 |
| 2018/0168443 A1 | 6/2018 | Inoue et al. |
| 2019/0290118 A1 | 9/2019 | Jha et al. |
| 2021/0259546 A1 * | 8/2021 | Santos Garcia ......... A61B 3/12 |

FOREIGN PATENT DOCUMENTS

| | | | | |
|---|---|---|---|---|
| CN | 109360653 A | * | 2/2019 | ............. G16H 50/20 |
| KR | 1020190034136 A | * | 4/2019 | |
| WO | 2010132304 | | 11/2010 | |
| WO | 2012162205 | | 11/2012 | |
| WO | 2018046957 | | 3/2018 | |
| WO | 2018064052 | | 4/2018 | |
| WO | WO-2019232579 A1 | * | 12/2019 | ........... A61B 5/6898 |

OTHER PUBLICATIONS

Machine translation of CN 109360653 A (Year: 2022).*
Unix & Linux StackExchange "What is/are the advantage(s) of running applications in background" Oct. 15, 2014 <https://unix.stackexchange.com/posts/162189/revisions> (Year: 2014).*
Pratt, et al. "Convolutional neural networks for diabetic retinopathy." Procedia computer science 90: 200-205. (Year: 2016).*
Real Time systems. In E. D. Reilly, A. Ralston, & D. Hemmendinger (Eds.), Encyclopedia of computer science (4th ed.). Wiley. Credo Reference: https://search.credoreference.com/content/entry/encyccs/real_time_systems/0?institutionId=743 (Year: 2003).*
Elliott et al., "Development of a Reading Speed Test for Potential-Vision Measurements," Investigative Ophthalmology & Visual Science, vol. 42, No. 8, Jul. 2001, pp. 1945-1949, 5 pages.
Ramulu et al., "Difficulty with Out-Loud and Silent Reading in Glaucoma," Investigative Ophthalmology & Visual Science, vol. 54, No. 1, Jan. 2013, pp. 666-672, 7 pages.
Fromer et al., "Are Individual Differences in Reading Speed Related to Extrafoveal Visual Acuity and Crowding?," PLOS One, DOI:10.1371/journal.pone.0121986, Mar. 19, 2015, 18 pages.
Walker et al., "The value of Tablets as reading aids for individuals with central visual field loss: an evaluation of eccentric reading with static and scrolling text," Ophthalmic & Physiological Optics, vol. 36, Issue 4, Jul. 2016, pp. 459-464, 6 pages.
Mell et al., "The NIST Definition of Cloud Computing," Recommendations of the National Institute of Standards and Technology, NIST Special Publication 800-145, Sep. 2011, 7 pages.
Non Final Office action received for U.S. Appl. No. 16/512,771 dated Jun. 29, 2021, 26 pages.
International Search Report and Written Opinion received for PCT application No. PCT/IB2020/056375 dated Oct. 21, 2020, 9 pages.

* cited by examiner

CONTINUAL BACKGROUND MONITORING OF EYE HEALTH

BACKGROUND

The subject disclosure relates to monitoring of eye health, and more specifically to continual background monitoring of eye health.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate continual background monitoring of eye health are described.

According to one or more embodiments, a system is provided. The system can comprise a memory that can store computer-executable components. The system can further comprise a processor that can be operably coupled to the memory and that can execute the computer-executable components stored in the memory. In various embodiments, the computer-executable components can comprise a sensor component of a device that can detect one or more physical characteristics associated with an entity. In various embodiments, the computer-executable components can further comprise a diagnostic component of the device that can estimate in a background of the device a health condition of an eye of the entity based on the one or more physical characteristics.

According to one or more embodiments, the above-described device can be implemented as a computer-implemented method and/or computer program product.

DETAILED DESCRIPTION

Figure 1A:
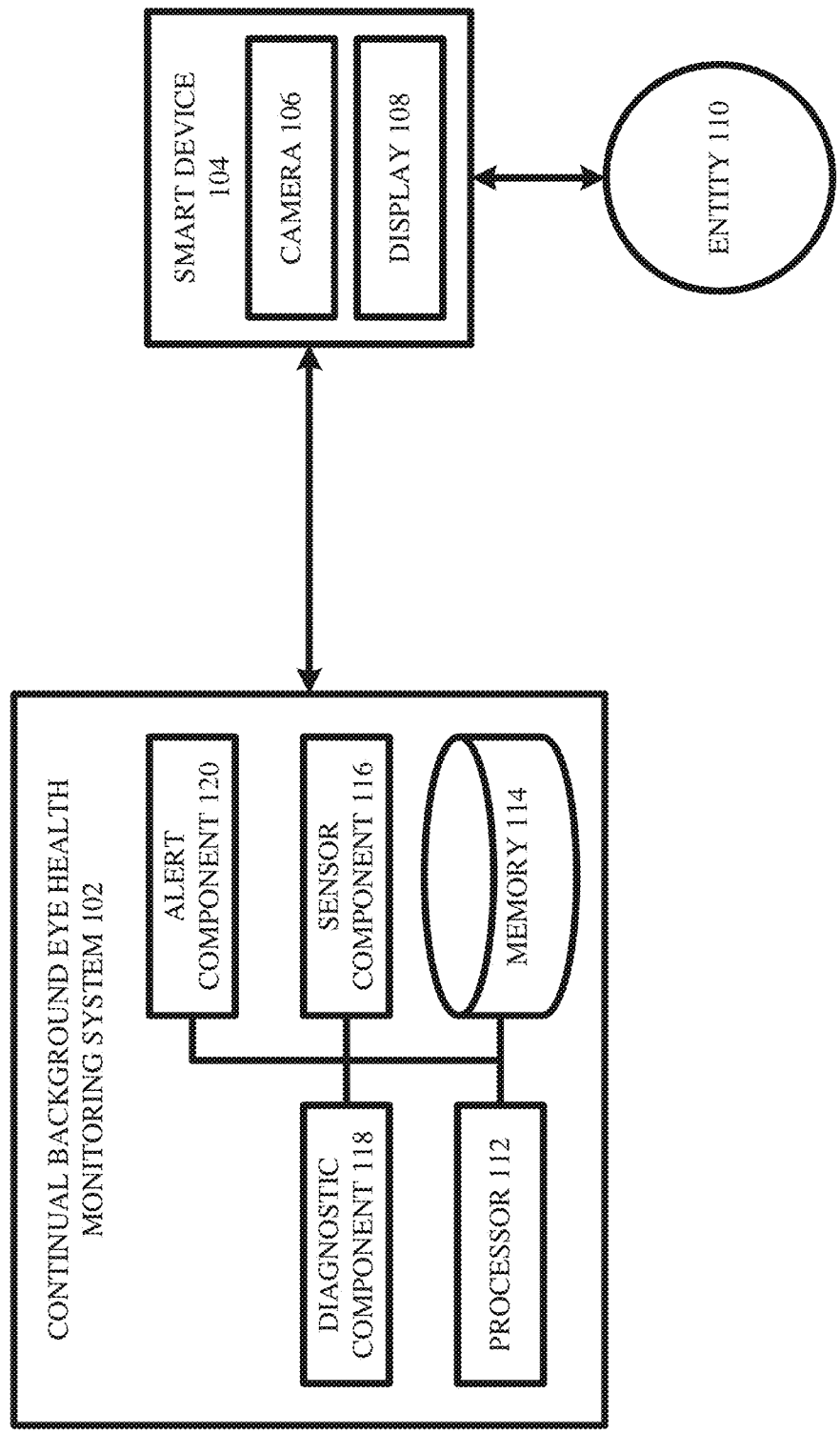
FIGS. 1*a*-1*b* illustrate a block diagram of an example, non-limiting system that facilitates continual background monitoring of eye health in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

On average, American adults spend over eleven hours per day listening to, watching, reading, or otherwise generally interacting with electronic media. More specifically, American adults spend, on average, about nine hours and fifteen minutes every day interacting with smart devices (e.g., smart phones, smart tablets, smart televisions, laptop computers, desktop computers, video game consoles). Smart devices generally comprise electronic visual displays (e.g., phone screens, tablet screens, computer screens, television screens, touch screens) to provide information to and/or receive input from users. Thus, users of smart devices are generally staring at electronic visual displays for long periods of time on a daily basis. Such prolonged use of smart devices can cause significant strain on a user's eyes, which can lead to discomfort and/or medical problems. Thus, preventative and/or medical diagnostic monitoring of eye health can be beneficial to diagnose, prevent, and/or treat medical problems relating to a user's eyes.

In various aspects, eye exams performed by an eye care professional (e.g., eye doctor) can be suboptimal. Specifically, it can often be difficult and/or costly to get an appointment with an eye care professional. Moreover, even if an eye exam from an eye care professional is successfully obtained, it is generally performed only once or twice a year. Furthermore, at-home eye exams that can be performed without medical professionals are time-consuming, require the user to take time out of their day to sit for the eye exam (e.g., which can interrupt the user's work and/or other activities), and require the user to remember to take and/or activate the eye exam in the first place (e.g., if the user forgets to sit for the exam or decides that time spent taking the exam might be better spent performing some other activity, no monitoring of eye health occurs). Further still, such eye exams evaluate the user's eye health at only a single instant in time. Thus, systems and/or techniques for automatically monitoring and/or diagnosing eye health of a user in the absence of medical professionals, in continuous and/or continual fashion, and/or without interrupting the user's daily activities can be beneficial. Various embodiments of the invention can solve one or more of these issues.

Embodiments described herein include systems, computer-implemented methods, apparatus, and/or computer program products that facilitate continual background monitoring of eye health. In various embodiments, an entity (e.g., a user) can interact with a smart device (e.g., a smart phone, a smart tablet, a smart television, a laptop or desktop computer). In various aspects, the smart device can comprise a camera. In various instances, the camera can face toward the entity while the entity interacts with the smart device (e.g., digital camera on a smart phone that is adjacent to the screen of the smart phone and that faces toward the entity when the entity views the screen of the smart phone; digital camera on a smart tablet that is adjacent to the screen of the smart tablet and that faces toward the entity when the entity views the screen of the smart tablet; digital camera on a smart television that is adjacent to the screen of the smart television and that faces toward the entity when the entity views the screen of the smart television; digital camera on a laptop or desktop computer that is adjacent to the screen of the laptop or desktop computer and that faces toward the entity when the entity views the screen of the laptop or desktop computer).

In various embodiments, the camera of the smart device can be leveraged to perform continual background monitoring of eye health of the entity. Specifically, various embodiments of the invention can be implemented as software on the smart device that, upon execution, causes the camera of the smart device to record images and/or videos of the eyes, face, and/or body of the entity. In various aspects, embodiments of the invention can include a trained machine learning classifier (e.g., artificial neural network, support vector machine, logistic regression classifier) that receives as input the recorded images and/or videos of the eyes, face, and/or body of the entity and produces as output a classification and/or label of the eye health of the entity (e.g., the trained machine learning classifier estimates, infers, determines, and/or diagnoses a medical health condition of the eye of the entity). The trained machine learning classifier can, in various aspects, employ any suitable artificial intelligence, machine learning, and/or deep learning paradigm (e.g., any suitable linear and/or non-linear techniques) to facilitate such classification and/or labeling.

In various aspects, embodiments of the invention can further comprise an alert component that can generate one or more alerts based on the outputted classification and/or label. In various instances, the alert component can display (e.g., on the screen of the smart device) the one or more alerts to the entity. In various cases, the one or more alerts can include medical diagnoses relating to the eyes of the entity, recommendations for addressing and/or preventing medical problems relating to the eyes of the entity (e.g., recommended treatments, recommended preventative measures, recommendation to visit an eye care professional), and/or descriptive statistics pertaining to the eye health of the entity.

In various instances, the eye health of the entity (e.g., the health condition relating to the eyes of the entity) can be based on one or more physical characteristics associated with the entity (e.g., one or more physical characteristics and/or physical symptoms exhibited by the eyes, face, and/or body of the entity). In various cases, the trained machine learning classifier can be trained to classify and/or label the eye health of the entity (e.g., can be trained to estimate, infer, determine, and/or diagnose the health condition of the eyes of the entity) based on any suitable number and/or any suitable types of physical characteristics. For instance, in various cases, the images and/or videos captured by the camera of the smart device can depict the one or more physical characteristics associated with the entity. In various embodiments, the trained machine learning classifier can be trained to receive the recorded images and/or videos as input, analyze the recorded images and/or videos to recognize the one or more physical characteristics, and classify and/or label the eye health of the entity (e.g., estimate, infer, determine, and/or diagnose a health condition of the eyes of the entity) based on the one or more physical characteristics. In various instances, the one or more physical characteristics can include eye movement and/or frequency of eye movement of the entity, blink rate of the entity, pupil contraction of the entity, pupil dilation of the entity, squinting of the eyes of the entity, wateriness of the eyes of the entity, redness of the eyes of the entity, facial expression of the entity, viewing angle of the entity in comparison to the font size and/or image size displayed by the smart device, posture of the entity, distance between the eyes of the entity and the camera and/or screen of the smart device in comparison to the font size and/or image size displayed by the smart device, and/or a change in any suitable physical characteristic over time. In various aspects, any other suitable physical characteristics and/or symptoms associated with the eyes, face, and/or body of the entity can be detected, captured, and/or recorded by the camera of the smart device and recognized, classified, and/or labeled by the trained machine learning classifier. In some cases, surrounding and/or ambient conditions can be detected by the smart device and used to help diagnose the health condition. For example, in some cases, the camera can detect ambient lighting levels and/or ambient temperature levels (e.g., via a thermographic camera and/or thermometer). In some cases, the trained machine learning classifier can be trained to classify the eye health of the entity (e.g., to estimate, infer, determine, and/or diagnose a health condition of the eyes of the entity) based in part on any other suitable input information pertaining to the entity (e.g., diet of the entity, body weight of the entity, age of the entity, prior and/or current medical conditions of the entity). In various cases, such input information can be received by various embodiments of the invention from the entity via any suitable interface device (e.g., touch screen, keyboard, key pad, voice recognition). In various cases, such input information can be received by various embodiments of the invention from any other suitable source (e.g., from electronic health records accessible by the smart device, such as from a health application).

Consider the following illustrative, non-limiting example. Suppose that an entity is interacting with a smart phone (e.g., browsing the internet on the smart phone, composing a text message or email on the smart phone, playing a video game on the smart phone). Furthermore, suppose that the entity's eyes are excessively red and watery (e.g., due to staring at the screen of the smart phone for too long without a break). While the entity is interacting with the smart phone, the camera of the smart phone can capture images and/or videos of the entity's eyes. Thus, the captured images and/or videos can depict the excessively red and watery eyes of the entity. In various cases, the trained machine learning classifier can receive as input the captured images and/or videos and produce as output a classification and/or label of the eye health of the entity (e.g., can estimate, infer, determine, and/or diagnose a health condition and/or medical condition relating to the eyes of the entity with which the entity appears to be afflicted). Since the captured images and/or videos depict the excessively red and watery eyes of the entity, the classification and/or label can indicate that the entity has excessively red and watery eyes. In other words, the trained machine learning classifier can facilitate image recognition (e.g., at one instant in time and/or over a period of time) of the captured images and/or videos to determine and/or infer that the entity has excessively red and watery eyes. Based on this classification/labeling of the eye health of the entity, embodiments of the invention can generate and display on the screen of the smart phone an appropriate alert that addresses the classified/labeled eye health of the entity (e.g., an alert that notifies the entity of the estimated, inferred, determined, and/or diagnoses health condition and suggests one or more mitigation solutions to treat/ameliorate the health condition). For instance, since the trained machine learning classifier determined/inferred that the entity has excessively red and watery eyes, the alert component can generate and display an alert that indicates to the entity that their eyes are excessively red and watery, that such redness and wateriness can indicate that the entity has been straining their eyes too much, and that the entity should accordingly cease looking at the screen of the smart phone (e.g., give their eyes a rest).

In some cases, the trained machine learning classifier can determine, based on the one or more physical characteristics depicted in the captured images and/or videos of the eyes, face, and/or body of the entity, that the entity is suffering from a known medical condition and/or disease that corresponds to the one or more physical characteristics. For instance, suppose that, in the above example, the entity had been looking at the screen of the smart phone for so long that the entity burst/ruptured an ocular blood vessel (e.g., the rupture can be visible on the sclera of the entity's eye). In such case, the camera of the smart phone can capture images and/or videos of the entity's eyes, and the trained machine learning classifier can analyze the captured images and/or videos to determine/infer that the entity has ruptured an ocular blood vessel. In other words, the trained machine learning classifier can recognize that the level and/or intensity of the redness of the entity's eyes corresponds more to a blood vessel rupture rather than to mere eye strain and/or tiredness. The alert component can accordingly generate and display an alert that indicates that the entity has burst/ruptured an ocular blood vessel and that indicates appropriate treatment and/or ameliorative measures for the entity to take (e.g., visit a doctor, apply eye drops, give eyes a rest).

Consider another illustrative, non-limiting example. Suppose that an entity is interacting with a laptop computer (e.g., browsing the internet on the laptop computer, composing a document or email on the laptop computer, playing a video game on the laptop computer). Furthermore, suppose that the entity frequently squints and rubs, itches, and/or scratches at their eyes while using the laptop computer (e.g., due to eye tiredness and/or blurriness). While the entity is interacting with the laptop computer, the camera of the laptop computer can capture images and/or videos of the entity's eyes, face, and/or body. Thus, the captured images and/or videos can depict the frequent squinting and rubbing, itching, and/or scratching of the entity's eyes. In various cases, the trained machine learning classifier can receive as input the captured images and/or videos and produce as output a classification and/or label of the eye health of the entity (e.g., can estimate, infer, determine, and/or diagnose a health condition relating to the eyes of the entity). Since the captured images and/or videos depict the frequent squinting and rubbing, itching, and/or scratching of the entity's eyes, the classification and/or label can indicate that the entity is frequently squinting and rubbing, itching, and/or scratching at their eyes. In other words, the trained machine learning classifier can facilitate image recognition (e.g., at one instant in time and/or over a period of time) of the captured images and/or videos to determine and/or infer that the entity is frequently squinting and rubbing, itching, and/or scratching at their eyes. Based on this classification/labeling of the eye health of the entity (e.g., based on the estimated, inferred, determined, and/or diagnosed health condition), the alert component can generate and display on the screen of the laptop computer an appropriate alert that addresses the classified/labeled eye health of the entity. For instance, since the trained machine learning classifier determined/inferred that the entity is frequently squinting and rubbing, itching, and/or scratching at their eyes, the alert component can generate and display an alert that indicates to the entity that they are frequently squinting and rubbing, itching, and/or scratching at their eyes, that such squinting and rubbing, itching, and/or scratching can indicate that the entity has been straining their eyes too much, and that the entity should accordingly cease looking at the screen of the laptop computer (e.g., give their eyes a rest).

Consider yet another illustrative, non-limiting example. Suppose that an entity is watching a smart television (e.g., watching a television show, watching a movie). Furthermore, suppose that the entity experiences a sudden onset of nystagmus (e.g., involuntary and erratic eye movement). While the entity is watching the smart television, the camera of the smart television can capture images and/or videos of the entity's eyes. Thus, the captured images and/or videos can depict the erratic movement of the entity's eyes. In various cases, the trained machine learning classifier can receive as input the captured images and/or videos and produce as output a classification and/or label of the eye health of the entity (e.g., can estimate, infer, determine, and/or diagnose a health condition relating to the eyes of the entity with which the entity appears to be afflicted). Since the captured images and/or videos depict the suddenly erratic movement of the entity's eyes, the classification and/or label can indicate that the entity is likely experiencing nystagmus. In other words, the trained machine learning classifier can facilitate image recognition (e.g., at one instant in time and/or over a period of time) of the captured images and/or videos to determine and/or infer that the entity's eyes are suddenly moving erratically. Since sudden and erratic movement of eyes can be correlated with nystagmus, the trained machine learning classifier can determine and/or infer that the entity is experiencing nystagmus. Based on this classification/labeling of the eye health of the entity, the alert component can generate and display on the screen of the smart television an appropriate alert that addresses the classified/labeled eye health of the entity (e.g., an alert that notifies the entity of the estimated, inferred, determined, and/or diagnosed health condition). For instance, since the trained machine learning classifier determined/inferred that the entity has nystagmus, the alert component can generate and display an alert that indicates to the entity that the entity is experiencing nystagmus, that nystagmus is a medical problem, and that a medical professional should be consulted.

In this way, various embodiments of the invention can leverage the camera of a smart device to facilitate eye health monitoring. In other words, the camera of the smart device can detect various, visually-perceptible symptoms relating to the entity's eyes, face, and/or body, and the trained machine learning classifier can determine, infer, and/or diagnose a behavior, a medical condition, and/or a disease that corresponds to the detected symptoms. In various instances, the trained machine learning classifier can be trained to recognize, classify, and/or label any suitable number and/or any suitable types of symptoms, behaviors, medical conditions, and/or diseases. Non-limiting examples of such symptoms, behaviors, medical conditions, and/or diseases can include erratic eye movement, increased and/or decreased eye movement, blink rate, increased and/or decreased blink rate, pupil dilation/contraction, increased and/or decreased pupil dilation/contraction, eye redness, increased and/or decreased eye redness, eye wateriness, increased and/or decreased eye wateriness, squinting, increased and/or decreased squinting, rubbing/itching/scratching of eyes, increased and/or decreased rubbing/itching/scratching of eyes, cloudiness of eyes, increased and/or decreased cloudiness, eye swelling, increased and/or decreased eye swelling, eye alignment, changes in eye alignment, myopia, hyperopia, keratoconus, nystagmus, cataracts, and/or any other suitable symptom/condition. In various instances, the trained machine learning classifier can be trained to detect, diagnose, recognize, and/or classify any suitable, visually-perceptible symptom and/or physical characteristic of the entity (e.g., any symptom that can be depicted in the images and/or videos captured by the camera of the smart device). In various aspects, the trained machine learning classifier can also be trained to recommend mitigation solutions (e.g., to suggest treatments to ameliorate the diagnosed health conditions).

Not only can various embodiments of the invention facilitate eye health monitoring, but various embodiments of the invention can do so in a processing background of the smart device. In various aspects, a background process can be a computing process that runs "behind the scenes" (e.g., in the background of the smart device) and that runs automatically without requiring active involvement/intervention from the entity and/or without interrupting other processes performed by the smart device. In various aspects, a background process can run substantially simultaneously with a non-background computing process. In such case, objects associated with the non-background computing process can be displayed on the screen of the smart device (e.g., graphical user interfaces, computing windows) so as to be in the entity's view, and objects associated with the background process can be not displayed on the screen of the smart device so as to be hidden from the entity's view.

Moreover, various embodiments of the invention can run continuously and/or continually in the background of the smart device. That is, in various aspects, embodiments of the invention can repeatedly perform health monitoring of the eyes of the entity (e.g., can repeatedly estimate, infer, determine, and/or diagnose a health condition of the eyes of the entity) at regular/periodic and/or irregular/aperiodic intervals. For instance, at a first point in time, various embodiments of the invention can capture first images and/or videos of the eyes, face, and/or body of the entity and analyze the first images and/or videos to classify and/or label the eye health of the entity at the first point in time. If needed, various embodiments of the invention can generate and display appropriate alerts to the user based on the first images and/or videos. In various aspects, various embodiments of the invention can repeat this process at a second point in time (e.g., can capture second images and/or videos of the eyes, face, and/or body of the entity and classify and/or label the eye health of the entity at the second point in time). In various aspects, this process can be repeated for any suitable number and/or spacing of points in time. In various aspects, any suitable regular and/or irregular time intervals can be implemented (e.g., the length of time between each iteration of eye health monitoring can be uniform and/or non-uniform; the length of time between each iteration of eye health monitoring can be any suitable length ranging from minutes, to seconds, to fractions of a second).

In this way, various embodiments of the invention can facilitate continual background monitoring of the eye health of the entity. In various aspects, continual background monitoring of eye health can provide many technical and practical, real-world benefits. For instance, continual monitoring can provide a much deeper and more complete insight into the eye health of the entity than can single, isolated eye exams that are performed once every several months. Specifically, while a single, isolated eye exam captures only the eye health of the entity at a particular point in time, continual monitoring can capture the time evolution of the eye health of the entity (e.g., can capture substantially all variations in the eye health of the entity over any suitable period of time). Moreover, monitoring the eye health of the entity in the background of the smart device can enable the entity's eyes to be monitored without interrupting the entity's normal use of the smart device. Specifically, since embodiments of the invention can run in the background of the smart device, the eye health of the entity can be monitored while the entity is using the smart device for other purposes and/or other activities (e.g., to work, to relax, to communicate). As explained herein, continual background monitoring of eye health can provide to an entity deeper and richer medical diagnostic information related to the entity's eyes, without requiring the entity to first make a costly appointment with an eye care professional, without interrupting the entity's normal use of their smart device, and without requiring the entity to purchase and/or otherwise obtain specialized medical diagnostic hardware/equipment (e.g., the comprehensive eye health monitoring described herein can be facilitated by any suitable smart device that is equipped with a camera).

For instance, consider the above example where the entity has red and watery eyes while interacting with a smart phone. As mentioned above, the entity can be using the smart phone for any suitable purpose, such as browsing the internet, composing a text message and/or email, playing a video game, interacting with social media, and/or facilitating video conferencing. In any of these scenarios, the entity is engaged in an activity (e.g., work and/or leisure) that utilizes the smart phone. Because various embodiments of the invention can facilitate continual background monitoring of eye health, various embodiments of the invention can monitor the eye health of the entity without interrupting the entity's current activities on the smart phone. Specifically, the camera of the smart phone can repeatedly capture images and/or videos of the eyes, face, and/or body of the entity while the entity is using the smart phone, and the trained machine learning classifier can analyze those captured images and/or videos to classify/label the eye health of the entity (e.g., to estimate, infer, determine, and/or diagnose a health condition of the eyes of the entity). In other words, since embodiments of the invention can run continually in a background of the smart phone, embodiments of the invention can capture and analyze the images and/or videos while the entity is browsing the internet on the smart phone, while the entity is composing a text message and/or email on the smart phone, while the entity is playing a video game on the smart phone, while the entity is interacting with social media on the smart phone, and/or while the entity is video conferencing on the smart phone. In this way, eye health monitoring can be facilitated without interrupting the activities of the entity (e.g., without requiring the entity to take work time and/or leisure time out of their day to sit for a discrete eye exam). In stark contrast, systems and/or techniques that monitor eye health with the smart phone but that do not operate in the background of the smart phone would require the entity to cease and/or interrupt their current activity in order to take an eye exam (e.g., the entity would have to stop browsing the internet, stop composing the text message and/or email, stop playing the video game, stop interacting with social media, and/or stop the video conference in order to sit for the eye exam). Thus, embodiments of the invention constitute a concrete technical improvement in the field of eye health monitoring and to the very functioning of smart devices.

Additionally, consider the above example where the entity frequently squints and rubs, itches, and/or scratches their eyes while interacting with a laptop computer. As mentioned above, the entity can be using the laptop computer for any suitable purpose, such as browsing the internet, composing a document and/or email, playing a video game, interacting with social media, and/or facilitating video conferencing. In any of these scenarios, the entity is engaged in an activity (e.g., work and/or leisure) that utilizes the laptop computer. Because various embodiments of the invention can facilitate continual background monitoring of eye health, various embodiments of the invention can monitor the eye health of the entity without interrupting the entity's current activities on the laptop computer. Specifically, the camera of the laptop computer can repeatedly capture images and/or videos of the eyes, face, and/or body of the entity while the entity is using the laptop computer, and the trained machine learning classifier can analyze those captured images and/or videos to classify/label the eye health of the entity (e.g., to estimate, infer, determine, and/or diagnose a health condition of the eyes of the entity). In other words, since embodiments of the invention can run continually in a background of the laptop computer, embodiments of the invention can capture and analyze the images and/or videos while the entity is browsing the internet on the laptop computer, while the entity is composing a document and/or email on the laptop computer, while the entity is playing a video game on the laptop computer, while the entity is interacting with social media on the laptop computer, and/or while the entity is video conferencing on the laptop computer. In this way, eye health monitoring can be facilitated without interrupting the activities of the entity (e.g., without requiring the entity to take work time and/or leisure time out of their day to sit for a discrete eye exam). In stark contrast, systems and/or techniques that monitor eye health with the laptop computer but that do not operate in the background of the laptop computer would require the entity to cease and/or interrupt their current activity in order to take an eye exam (e.g., the entity would have to stop browsing the internet, stop composing the document and/or email, stop playing the video game, stop interacting with social media, and/or stop the video conference in order to sit for the eye exam). Thus, embodiments of the invention constitute a concrete technical improvement in the field of eye health monitoring and to the very functioning of smart devices.

Furthermore, consider the above example where the entity experiences a sudden onset of nystagmus while interacting with a smart television. As mentioned above, the entity can be using the smart television for any suitable purpose, such as watching a television show or watching a movie. In any of these scenarios, the entity is engaged in an activity (e.g., work and/or leisure) that utilizes the smart television. Because various embodiments of the invention can facilitate continual background monitoring of eye health, various embodiments of the invention can monitor the eye health of the entity without interrupting the entity's current activities on the smart television. Specifically, the camera of the smart television can repeatedly capture images and/or videos of the eyes, face, and/or body of the entity while the entity is using the smart television, and the trained machine learning classifier can analyze those captured images and/or videos to classify/label the eye health of the entity (e.g., to estimate, infer, determine, and/or diagnose a health condition of the eyes of the entity). In other words, since embodiments of the invention can run continually in a background of the smart television, embodiments of the invention can capture and analyze the images and/or videos while the entity is watching the television show or movie. In this way, eye health monitoring can be facilitated without interrupting the activities of the entity (e.g., without requiring the entity to take work time and/or leisure time out of their day to sit for a discrete eye exam). In stark contrast, systems and/or techniques for monitoring eye health that do not operate in the background of the smart television would require the entity to cease and/or interrupt their current activity in order to take an eye exam (e.g., the entity would have to stop watching the television show or movie). Thus, embodiments of the invention constitute a concrete technical improvement in the field of eye health monitoring and to the very functioning of smart devices.

In various aspects, embodiments of the invention can include a feedback component that can receive feedback from the entity regarding the helpfulness and/or accuracy of the outputted classifications/labels and/or the displayed alerts. In this way, various embodiments of the invention can facilitate active learning based on the feedback from the entity (e.g., feedback from the entity can be used to improve and/or customize the diagnostic accuracy of the trained machine learning classifier). As mentioned above, the trained machine learning classifier can be pre-trained via supervised, unsupervised, and/or reinforcement learning to receive as input captured images and/or videos of the eyes, face, and/or body of the entity and to produce as output a classification/label of the eye health of the entity (e.g., to estimate, infer, determine, and/or diagnose a health condition relating to the eyes of the entity) based on the captured images and/or videos. In other words, the trained machine learning classifier can be trained to recognize, classify, and/or label symptoms, behaviors, medical conditions, and/or diseases that correspond to physical symptoms and/or physical behaviors depicted in the captured images and/or videos. In various aspects, the diagnostic capabilities of the trained machine learning classifier can be further improved through active learning based on the feedback from the entity. For example, the feedback from the entity can indicate that a classification/label outputted by the trained machine learning classifier was incorrect and can further indicate what the correct classification/label would have been. Based on this feedback, backpropagation and/or any other suitable updating technique can be used to improve the parameters (e.g., weights and/or biases) of the trained machine learning classifier. In this way, various embodiments of the invention can learn from mistaken classifications/labels. In some instances, the feedback can be used to facilitate supervised learning. In other instances, the feedback can be used to facilitate any other suitable type of learning (e.g., unsupervised, reinforcement).

In some cases, the feedback can further indicate what types and/or manners of alerts the entity desires to receive (e.g., the feedback can indicate that the entity desires to receive only video alerts, audio alerts, and/or tactile alerts; the feedback can indicate that the entity desires to receive alerts regarding only certain medical conditions). In this way, the feedback can, in some cases, be used by the entity to subscribe to and/or unsubscribe from different types of alerts.

In various aspects, active learning can be further facilitated by a centralized knowledge base. In various instances, a centralized knowledge base can be a database that contains the feedback from multiple entities interacting with multiple smart devices (e.g., feedback from other users of various embodiments of the invention). The centralized knowledge base can facilitate more robust active learning by incorporating feedback from many, separate entities across many, separate smart devices. For example, suppose that entity A has a smart phone that can facilitate continual background monitoring of eye health and that entity B has a desktop computer that can facilitate continual background monitoring of eye health. Further, suppose that the smart phone of entity A has not incorrectly classified/labeled a health condition of entity A, while the desktop computer of entity B has incorrectly classified/labeled a health condition of entity B. If entity B provides feedback (e.g., indicating that the outputted classification was incorrect and indicating what the correct classification would have been), that feedback can be transmitted to and/or stored in the centralized knowledge base and active learning can be facilitated on every instance and/or version of the invention that has access to the centralized knowledge base. Thus, both the trained machine learning classifier of the smart phone of entity A and the trained machine learning classifier of the desktop computer of entity B can be updated based on entity B's feedback (e.g., the smart phone of entity A can learn from the mistake of the desktop computer of entity B). In this way, active learning can be facilitated across different entities and across different smart devices (e.g., smart devices that are communicatively coupled to the centralized knowledge base).

In various instances, embodiments of the invention can comprise a profile component that can generate an eye health profile corresponding to the entity and can share the eye health profile across multiple smart devices used by the entity. In various aspects, the eye health profile of the entity can be an electronic file and/or document that stores and/or records the health conditions classified, labeled, estimated, inferred, determined, and/or diagnosed by the trained machine learning classifier, the alerts generated and/or displayed by the alert component, feedback received by the feedback component, and/or metadata regarding any of the aforementioned (e.g., time stamps, smart device identifiers, smart device processing logs). Since the eye health profile can be shared among multiple smart devices used by the entity, a comprehensive history of the entity's eye health can be tracked across different smart devices. For example, suppose that an entity uses a smart phone for a first time period and then uses a smart television for a second time period. The smart phone can, in various aspects, facilitate continual background monitoring of eye health during the first time period. That is, during the first time period, the smart phone can update the eye health profile of the entity. Similarly, the smart television can facilitate continual background monitoring of eye health during the second time period. That is, during the second time period, the smart television can update the eye health profile of the entity. In this way, the smart television, which is operated during the second time period, can have access to pertinent eye health information regarding the entity that was generated and/or recorded by the smart phone during the first time period. Thus, in various aspects, embodiments of the invention can track usage and/or vision health of the entity across multiple smart devices.

In some cases, a smart device can be used by more than one entity. In such cases, embodiments of the invention can employ facial recognition in order to identify the entity currently using the smart device. In this way, the correct eye health profile can be accessed and updated at any given time.

In various aspects, embodiments of the invention can provide medical diagnostic capabilities for monitoring eye health comprehensively over a long period of time in order to provide early detection of eye diseases and/or eye struggle/strain. In various aspects, embodiments of the invention can be facilitated on any suitable smart device that includes a camera. Thus, in various instances, eye health monitoring that facilitates early detection of and/or suggested treatment for eye diseases and/or eye strain/struggle can be provided to patients/users that do not visit the optometrist regularly and/or that have no access to an eye doctor. In other words, embodiments of the invention can give standard smart devices(e.g., smart phones, smart tablets, smart televisions, laptops/desktops) the capability to comprehensively and reliably detect, diagnose, and/or suggest treatments for medical conditions/diseases related to the eyes of the user of the smart device. Via various embodiments of the invention, medical diagnosis of eye diseases can be facilitated without requiring costly trips to the eye doctor, without requiring specialized medical diagnostic hardware, and/or without interrupting the user's interaction with their smart device.

Various embodiments of the invention can be employed to use hardware and/or software to solve problems that are highly technical in nature (e.g., to facilitate continual background monitoring of eye health), that are not abstract and that cannot be performed as a set of mental acts by a human. Further, some of the processes performed can be performed by a specialized computer (e.g., trained machine learning classifier) for carrying out defined tasks related to continual background monitoring of eye health (e.g., detecting one or more physical characteristics associated with the eyes, face, and/or body of an entity via a camera of a smart device; continually estimating, by a trained machine learning classifier, in a background of the smart device a health condition of the entity based on the one or more physical characteristics; generating and displaying, on a screen of the smart device, one or more alerts based on the health condition). Such defined tasks are not conventionally performed manually by humans. Moreover, neither the human mind nor a human with pen and paper can continually estimate in a background of a smart device a health condition of an entity. Instead, various embodiments of the invention are inherently and inextricably tied to computer technology and cannot be implemented outside of a computing environment. In various instances, embodiments of the invention can integrate into a practical application the disclosed teachings regarding continual background monitoring of eye health. Indeed, in various embodiments, the disclosed teachings can enhance the functionality of smart devices by enabling them to monitor/diagnose health conditions/diseases of an eye of an entity without interrupting the entity's use of the smart device (e.g., can facilitate reliable monitoring/diagnosis of vision health without requiring the entity to cease their current activity on the smart device). This is clearly a useful and practical application of computers/smart devices. Moreover, various embodiments of the invention can provide technical improvements to and solve problems that arise in the field of eye health monitoring. After all, because various embodiments of the invention run continually in a processing background of the smart device, embodiments of the invention provide more convenient and more robust eye health monitoring capabilities than can existing systems/techniques that monitor eye health (e.g., embodiments of the invention can provide a comprehensive time evolution of the visual health of an entity recorded across multiple smart devices with which the entity normally interacts without interrupting the entity's use of those multiple smart devices). Furthermore, various embodiments of the invention can control real-world devices based on the disclosed teachings. For example, embodiments of the invention can leverage a real-world camera of a real-world smart device (e.g., smart phone, smart tablet, smart television, laptop/desktop) to capture images and/or videos of the real-world eyes, face, and/or body of a real-world entity (e.g., user of the smart device). Moreover, embodiments of the invention can leverage a real-world machine learning classifier to classify/label a health condition of the eyes of the entity based on the captured images and/or videos. Furthermore, embodiments of the invention can generate and display real-world alerts on the real-world screen of the smart device to the entity based on the health condition (e.g., notifying the entity of pertinent medical diagnoses). Further still, in various aspects, various embodiments of the invention can contact, schedule and/or otherwise procure medical professional services for the entity based on the generated and displayed alert (e.g., if the trained machine learning classifier and/or the alert component determines that a doctor should be consulted, embodiments of the invention can automatically contact a nearby doctor's office to schedule an appointment for the entity). Such embodiments thus constitute a concrete and tangible technical improvement in the field of eye health monitoring.

FIG. 1a illustrates a block diagram of an example, non-limiting system 100a that can facilitate continual background monitoring of eye health in accordance with one or more embodiments described herein. As shown, a continual background eye health monitoring system 102 can leverage a smart device 104 in order to continually monitor the eye health of an entity 110. In various instances, the entity 110 can be any suitable living organism and/or living creature having an eye for which health monitoring is desired (e.g., human, animal). In various embodiments, the entity 110 can be a human user of the smart device 104 whose eye health can be monitored/diagnosed while the entity 110 uses the smart device 104. In various other embodiments, as shown in FIG. 1b, the entity 110 can be separate from a user, operator, and/or controller of the smart device 104.

Figure 1B:
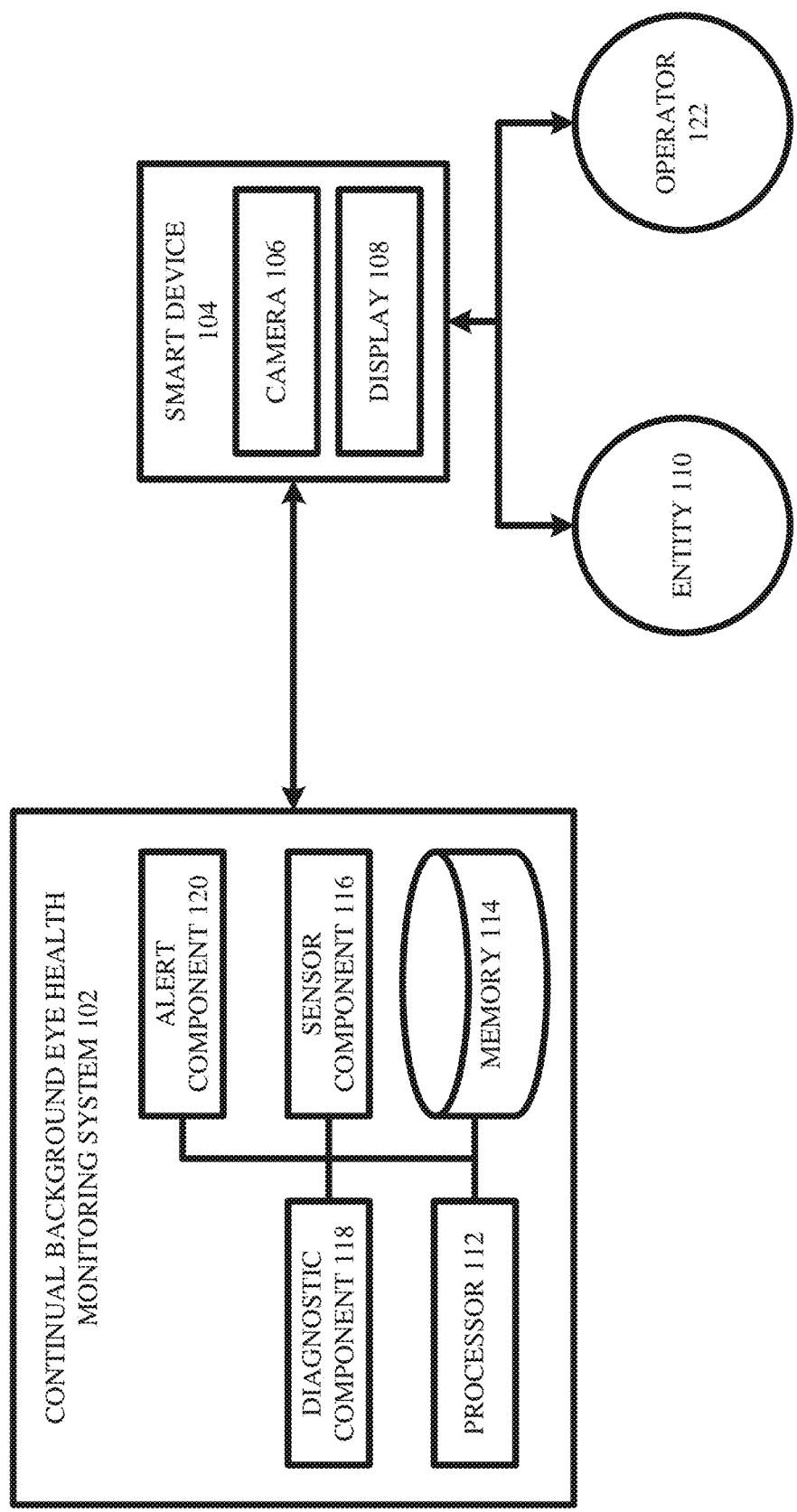

FIG. 1b illustrates a block diagram of an example, non-limiting system 100b that can facilitate continual background monitoring of eye health in accordance with one or more embodiments described herein. As shown, the system 100b can, in various instances, comprise the same components as the system 100a, and can further comprise an operator 122. In various instances, the operator 122 can control, use, and/or operate the smart device 104 to facilitate monitoring/diagnosing of the eye health of the entity 110. In various cases, the operator 122 can be any suitable device, machine, component having artificial intelligence capabilities and/or programming, and/or any other suitable operator, human or otherwise, of the smart device 104. For example, in some cases, the operator 122 can be an eye care professional (e.g., a doctor) and the entity 110 can be a patient of the eye care professional. In such cases, the operator 122 (e.g., the doctor) can control the smart device 104 so as to facilitate monitoring of the eye health of the entity 110 (e.g., the patient). In various embodiments, the entity 110 (e.g., the living organism whose eye health is monitored/diagnosed by the smart device 104 via the continual background eye health monitoring system 102) can be separate and/or distinct from the operator 122 (e.g., the human and/or machine that uses, controls, and/or operates the smart device 104 and/or the continual background eye health monitoring system 102), as shown in FIG. 1b. In various other embodiments, the entity 110 (e.g., the living organism whose eye health is monitored/diagnosed by the continual background eye health monitoring system 102) can be the same as the operator 122 (e.g., the human and/or machine that uses, controls, and/or operates the smart device 104 and/or the continual background eye health monitoring system 102), as shown in FIG. 1a (e.g., the controller, operator, and/or user of the smart device 104 can be the living organism whose eye health is to be monitored).

Although the remaining figures and disclosure elaborate upon the system depicted in FIG. 1a, this is exemplary, non-limiting, and for sake of brevity. In various cases, any aspects and/or details described herein as being implemented in embodiments of the invention that do not include the operator 122 can, in various instances, be implemented in embodiments of the invention that do include the operator 122.

In various aspects, the smart device 104 can be any suitable smart device with which the entity 110 can interact and that comprises a camera 106 and/or a display 108. In various aspects, the camera 106 can be any suitable electronic and/or digital camera that can record and/or capture images and/or videos. In various aspects, the display 108 can be any suitable electronic and/or digital display screen and/or monitor that can display images and/or videos to the entity 110. In various non-limiting examples, the smart device 104 can be a smart phone, a smart tablet, a smart television, a laptop computer, a desktop computer, a gaming console, and/or any other suitable smart device that includes a camera and an electronic display screen. In various embodiments, the camera 106 and the display 108 can be physically arranged in any suitable configuration such that the entity 110 can view/see the display 108 when using the smart device 104 and such that the camera 106 can face toward the entity 110 when the entity 110 is using the smart device 104. Although the herein figures depict the smart device 104 as having only one camera 106 and only one display 108, it should be appreciated that this is for illustration only. In various aspects, the smart device 104 can have any suitable numbers and/or types of cameras 106 and/or any suitable numbers and/or types of displays 108 physically arranged in any suitable configuration.

In various aspects, the continual background eye health monitoring system 102 can be communicatively coupled to the smart device 104 via any suitable wired and/or wireless electronic connection.

In various embodiments, the continual background eye health monitoring system 102 can comprise a processor 112 (e.g., computer processing unit, microprocessor) and a computer-readable memory 114 that is operably connected to the processor 112. The memory 114 can store computer-executable instructions which, upon execution by the processor 112, can cause the processor 112 and/or other components of the continual background eye health monitoring system 102 (e.g., sensor component 116, diagnostic component 118, alert component 120) to perform one or more acts. In various embodiments, the memory 114 can store computer-executable components (e.g., sensor component 116, diagnostic component 118, alert component 120), and the processor 112 can execute the computer-executable components.

In various embodiments, the continual background eye health monitoring system 102 can comprise a sensor component 116. In various aspects, the sensor component 116 can detect one or more physical characteristics associated with the entity 110 (e.g., later shown as numeral 302 in FIG. 3). In various instances, the sensor component 116 can leverage the camera 106 of the smart device 104 to detect the one or more physical characteristics associated with the entity 110. For instance, suppose that the entity 110 is interacting with the smart device 104 (e.g., browsing the internet; composing a document, email, and/or text message; watching videos on social media; reading electronically stored articles and/or e-books; participating in a video conference). While the entity 110 is interacting with the smart device 104, the sensor component 116 can cause the camera 106 of the smart device 104 to capture and/or record images and/or videos of the entity 110 (e.g., capture and/or record images and/or videos of the eyes, face, and/or body of the entity 110). Since the captured images and/or videos can depict the eyes, face, and/or body of the entity 110, the captured images and/or videos can depict physical characteristics exhibited by the entity 110 (e.g., can depict physical and/or visually-perceptible symptoms and/or behaviors exhibited by the eyes, face, and/or body of the entity 110). Some non-limiting examples of physical characteristics that can be captured/detected by the sensor component 116 (e.g., that can be depicted in the images and/or videos recorded by the camera 106) can include movement of the eyes of the entity 110, changes in the movement of the eyes of the entity 110, blink rate of the entity 110, changes in the blink rate of the entity 110, pupil dilation/contraction of the entity 110, changes in the pupil dilation/contraction of the entity 110, redness of the eyes of the entity 110, changes in the redness of the eyes of the entity 110, wateriness of the eyes of the entity 110, changes in the wateriness of the eyes of the entity 110, squinting of the eyes of the entity 110, changes in the squinting of the eyes of the entity 110, rubbing/itching/scratching of the eyes of the entity 110, changes in the rubbing/itching/scratching of the eyes of the entity 110, cloudiness of the eyes of the entity 110, changes in the cloudiness of the eyes of the entity 110, swelling of the eyes of the entity 110, changes in the swelling of the eyes of the entity 110, alignment of the eyes of the entity 110, changes in the alignment of the eyes of the entity 110, facial expression of the entity 110, changes in the facial expression of the entity 110, posture of the entity 110, changes in the posture of the entity 110, distance between the eyes of the entity 110 and the camera 106 and/or display 108, changes in the distance between the eyes of the entity 110 and the camera 106 and/or display 108, viewing angle of the entity 110, changes in the viewing angle of the entity 110, and/or any other suitable symptom/characteristic. In some cases, the sensor component 116 can detect ambient conditions of the smart device 104 (e.g., ambient lighting can be detected via the camera 106, ambient temperature can be detected by an electronic temperature sensor in the smart device 104 and/or by the camera 106 when thermographic technology is implemented).

In various embodiments, the continual background eye health monitoring system 102 can comprise a diagnostic component 118. In various aspects, the diagnostic component 118 can continually estimate in a background of the smart device 104 a health condition of an eye of the entity 110. In various instances, the diagnostic component 118 can leverage a trained machine learning classifier (e.g., later shown as numeral 402 in FIG. 4) to analyze the one or more physical characteristics detected by the sensor component 116 and estimate, determine, infer, and/or diagnose a health condition with which the entity 110 is seemingly afflicted. In other words, the diagnostic component 118 can receive as input the images and/or videos captured by the camera 106, can analyze the captured images and/or videos to recognize the one or more physical characteristics depicted in the captured images and/or videos, and can generate as output a classification and/or label characterizing the eye health of the entity 110 based on the one or more physical characteristics. In various aspects, the diagnostic component 118 can be considered as recognizing in the captured images and/or videos one or more physical symptoms exhibited by the entity 110 and identifying/determining/diagnosing those symptoms and/or a medical condition corresponding to those symptoms. For instance, if the images and/or videos received by the sensor component 116 depict the entity 110 as having excessively red and watery eyes, the diagnostic component 118 can analyze the images and/or videos to estimate, determine, infer, and/or diagnose that the entity 110 has excessively red and watery eyes. Since excessively red and watery eyes can be correlated with excessive eye strain, the diagnostic component 118 can determine that the eyes of the entity 110 are excessively strained. As another example, if the images and/or videos received by the sensor component 116 depict the entity 110 as excessively rubbing his/her eyes, the diagnostic component 118 can analyze the images and/or videos to estimate, determine, infer, and/or diagnose that the entity 110 is excessively rubbing his/her eyes. Since excessive rubbing of eyes can be correlated with eye tiredness and/or blurriness, the diagnostic component 118 can determine that the eyes of the entity 110 are excessively tired and/or blurry. As yet another example, if the images and/or videos received by the sensor component 116 depict the entity 110 as squinting excessively and sitting too near the display 108, the diagnostic component 118 can analyze the images and/or videos to estimate, determine, infer, and/or diagnose that the entity 110 is squinting excessively and staring too closely at the display 108. Since excessive squinting and being too close to the display 108 can be correlated with myopia (e.g., nearsightedness), the diagnostic component 118 can determine/infer that the entity 110 has myopia.

In various aspects, the sensor component 116 and the diagnostic component 118 can operate continuously and/or continually in a processing/computing background of the smart device 104. As mentioned above, continual operation can be characterized by repeated and/or periodic health monitoring at regular and/or irregular intervals of any suitable time span (e.g., minutes, seconds, tenths of a second, hundredths of a second, milliseconds). That is, in various aspects, the sensor component 116 can receive newly captured/recorded images and/or videos of the entity 110 at each time interval, and the diagnostic component 118 can analyze the newly captured/recorded images and/or videos to determine a health condition of the eyes of the entity 110 for each time interval. By incorporating continual monitoring of eye health (e.g., with time intervals on the order of minutes, seconds, and/or fractions of a second), embodiments of the invention can generate more complete and more accurate diagnostic information than can conventional systems/techniques (e.g., conventional eye exams capture eye health at a single instant in time, while continual monitoring can capture the more granular temporal evolution of eye health in real-time). Moreover, since the sensor component 116 and the diagnostic component 118 can operate in a processing background of the smart device 104, they can operate without interrupting use of the smart device 104 by the entity 110. That is, in various aspects, the entity 110 can be using and/or interacting with the smart device 104 (e.g., browsing the internet on the smart device 104, composing a document/message/email on the smart device 104, reading and/or watching electronic media on the smart device 104, video conferencing on the smart device 104), the sensor component 116 can capture images and/or videos of the eyes, face, and/or body of the entity 110 while the entity 110 is using and/or interacting with the smart device 104, and the diagnostic component 118 can analyze the captured images and/or videos to diagnose a health condition of the eyes of the entity 110 while the entity 110 is using and/or interacting with the smart device 104. In other words, the continual background eye health monitoring system 102 can capture images and/or videos of the entity 110 and can diagnose the eye health of the entity 110 without interrupting the entity's use of the smart device 104 (e.g., such that the eye health of the entity 110 is monitored without requiring the entity 110 to stop browsing the internet on the smart device 104, to stop composing the document/message/email on the smart device 104, to stop reading and/or watching the electronic media on the smart device 104, or to stop video conferencing with smart device 104).

In various embodiments, the continual background eye health monitoring system 102 can comprise an alert component 120. In various aspects, the alert component 120 can generate an alert based on the estimated, determined, inferred, and/or diagnosed health condition of the eyes of the entity 110. In various instances, the alert component 120 can display the alert to the entity 110 on the display 108 (e.g., on a screen of the smart device 104). In some embodiments, the alert can include video, audio, and/or tactile components (e.g., a visual alert displayed to the entity 110 on the display 108, an auditory/audible alert presented to the entity 110 via a speaker of the smart device 104, a tactile/vibratory alert presented to the entity 110 via a vibration generator of the smart device 104). In various aspects, the alert generated and displayed by the alert component 120 can comprise diagnoses and/or recommendations (e.g., later shown as numeral 502 in FIG. 5) related to the estimated, determined, inferred, and/or diagnosed health condition of the eyes of the entity. For example, the alert can indicate to the entity 110 the identity of an affliction, disease, and/or medical condition of the eyes of the entity 110 (e.g., can indicate that the entity 110 has ruptured an ocular blood vessel, can indicate that the eyes of the entity 110 are excessively red and watery, can indicate that the entity 110 is experiencing erratic eye movement which suggests a decrease in visual field) and can also indicate suggested treatments and/or actions to take to ameliorate the affliction, disease, and/or medical condition (e.g., can recommend visiting an eye care professional, can recommend ceasing use of the smart device 104, can recommend applying eye drops). In various aspects, the alert can comprise descriptive statistics (e.g., later shown as 504 in FIG. 5) that characterize the eye health of the entity 110. Non-limiting examples of such statistics can include blink rate, frequency of eye movement, screen time, squinting rate, watery eye rate, posture of the entity 110, distance between the entity 110 and the display 108, and/or any other suitable descriptive statistic. In various aspects, if the alert component suggests consulting an eye care professional, the alert component can electronically contact an eye care professional near the entity 110 (e.g., can electronically procure an appointment with a nearby eye doctor for the entity 110 and/or provide the nearby eye doctor with the diagnosed health condition of the entity 110).

Figure 2:
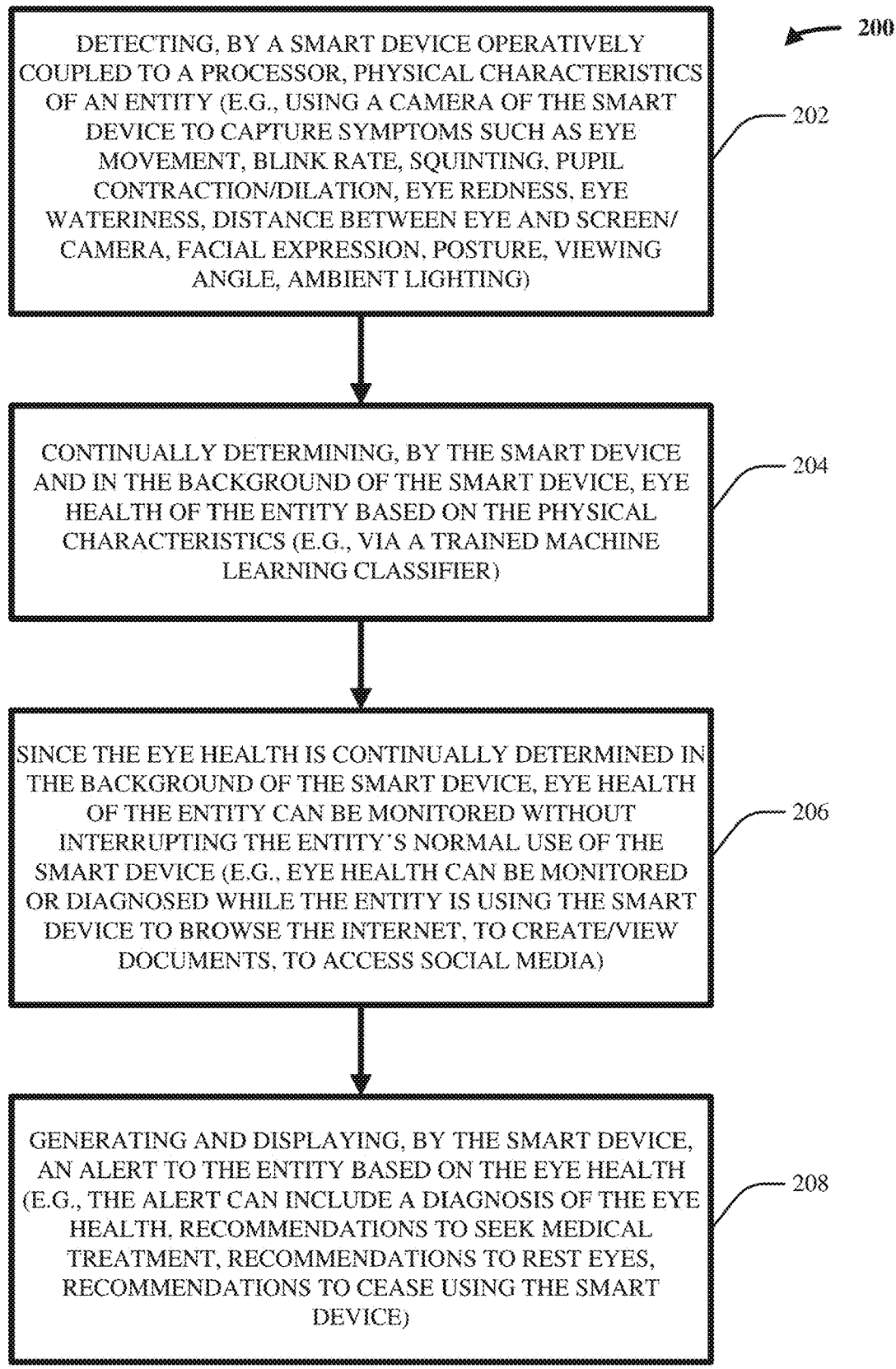
FIG. 2 illustrates a flow diagram of an example, non-limiting computer-implemented method that facilitates continual background monitoring of eye health in accordance with one or more embodiments described herein.

FIG. 2 illustrates a flow diagram of an example, non-limiting computer-implemented method 200 that can facilitate continual background monitoring of eye health in accordance with one or more embodiments described herein. In various aspects, the computer-implemented method 200 can be implemented by the system 100a and/or the system 100b.

In various embodiments, act 202 can include detecting, by a smart device (e.g., 116 and 104) operatively coupled to a processor, physical characteristics of an entity (e.g., 110). For instance, this can include using a camera (e.g., 106) of the smart device to capture symptoms of the entity such as eye movement, blink rate, squinting, pupil contraction/dilation, eye redness, eye wateriness, distance between the eyes of the entity and the screen or camera of the smart device, facial expression of the entity, posture of the entity, viewing angle of the entity, ambient lighting, and/or any other suitable visually-perceptible symptoms of the entity.

In various aspects, act 204 can include continually determining, by the smart device and in a background of the smart device (e.g., 118 and 104), eye health of the entity based on the physical characteristics. For instance, this can be facilitated by a trained machine learning classifier.

In various instances, as shown in numeral 206, since the eye health is continually determined in the background of the smart device, the eye health of the entity can be monitored without interrupting the entity's normal use of the smart device. For example, the eye health of the entity can be monitored or diagnosed while the entity is using the smart device to browse the internet, to create/view documents, and/or to access social media.

In various cases, act 208 can include generating and displaying, by the smart device (e.g., 120 and 104), an alert to the entity based on the diagnosed eye health. For instance, the alert can include a diagnosis of the eye health, can include recommendations to seek medical treatment, and/or can include recommendations to cease using the smart device.

Figure 3:
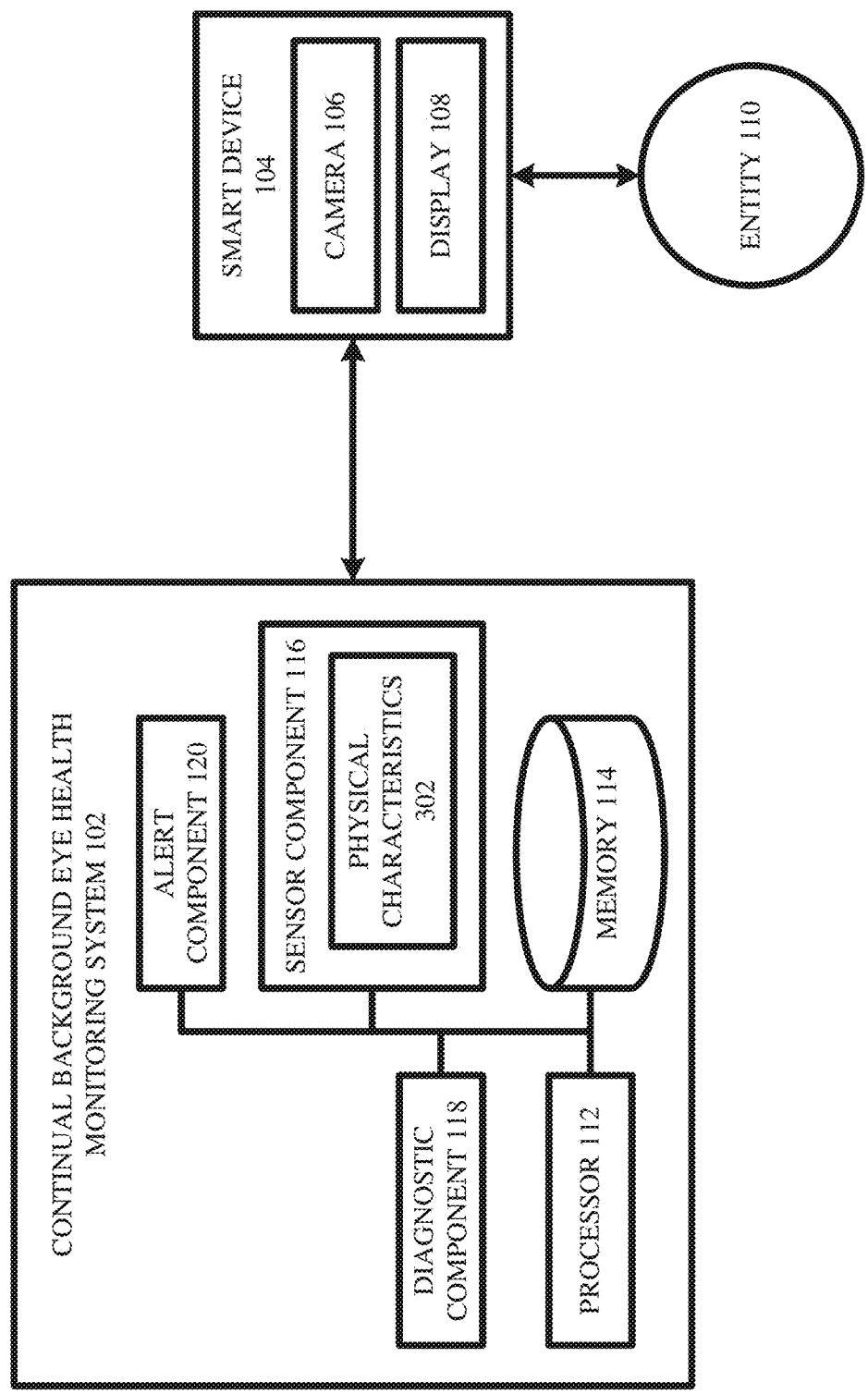
FIG. 3 illustrates a block diagram of an example, non-limiting system including physical characteristics that facilitates continual background monitoring of eye health in accordance with one or more embodiments described herein.

FIG. 3 illustrates a block diagram of an example, non-limiting system 300 including physical characteristics that can facilitate continual background monitoring of eye health in accordance with one or more embodiments described herein. As shown, the system 300 can, in various aspects, comprise the same components as the system 100a and/or the system 100b, and can further comprise physical characteristics 302.

As explained above, the sensor component 116 can leverage the camera 106 of the smart device 104 in order to capture/record images and/or videos of the eyes, face, and/or body of the entity 110. In various cases, these captured/recorded images and/or videos can depict one or more physical characteristics 302 of the entity 110 (e.g., one or more physical symptoms and/or behaviors exhibited by the eyes, face, and/or body of the entity 110). As explained above, the physical characteristics 302 can, in various aspects, include any suitable, visually-perceptible symptoms and/or behaviors exhibited by the entity 110 and/or changes in symptoms and/or behaviors exhibited by the entity 110 (e.g., eye position, eye movement, blink rate, pupil contraction/dilation, eye redness, eye wateriness, eye cloudiness, squinting, rubbing/itching/scratching of eyes, eye swelling, eye alignment, facial expression, viewing angle, posture, distance between eyes of the entity 110 and the display 108, ambient lighting). Based on the physical characteristics 302, the continual background eye health monitoring system 102 can, via the diagnostic component 118, diagnose, estimate, determine, and/or infer the eye health of the entity 110 (e.g., the diagnostic component 118 can recognize/identify the symptoms/behaviors depicted in the recorded images and/or videos, and/or can diagnose medical conditions that correspond to the depicted symptoms/behaviors).

Figure 4:
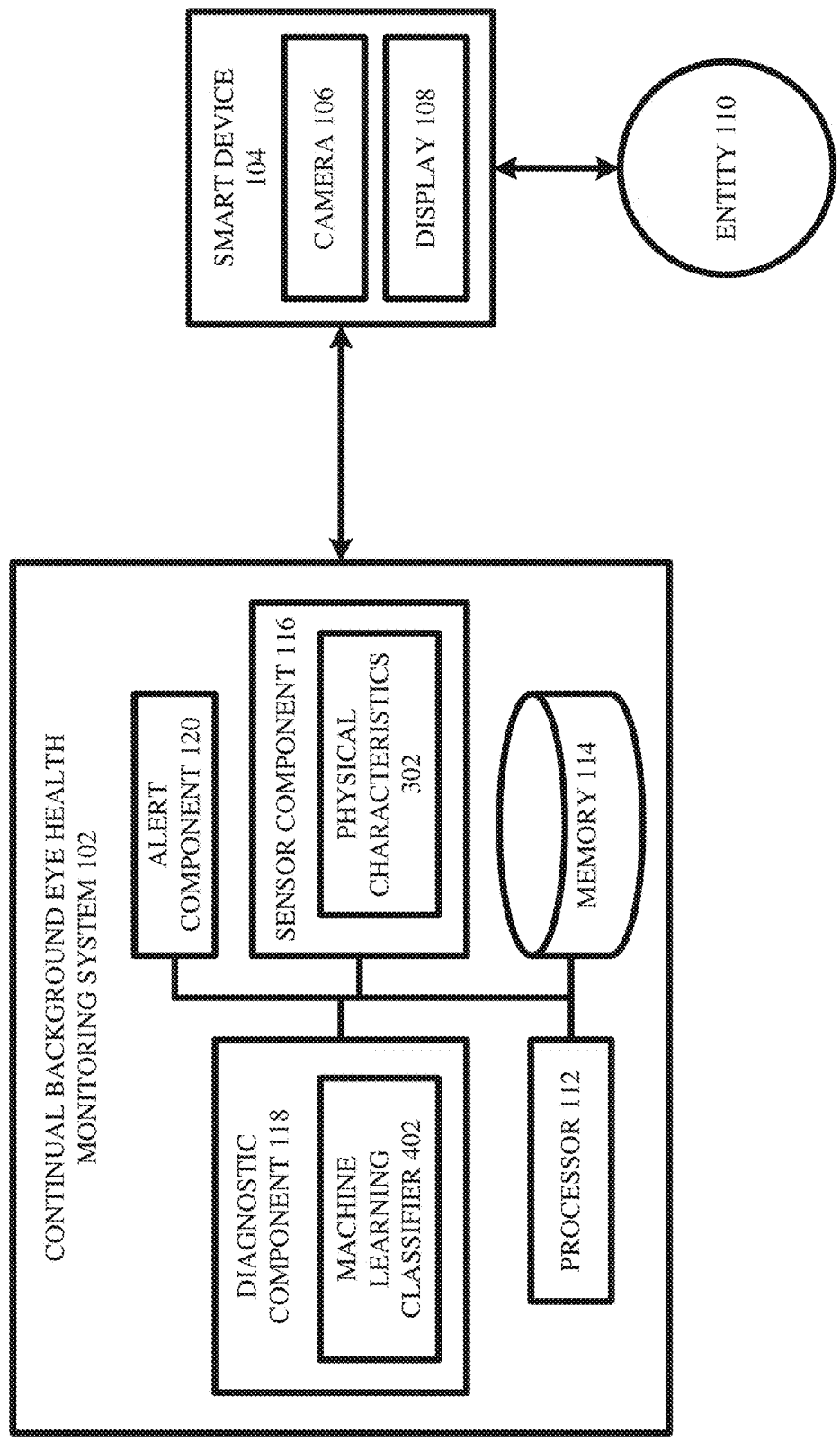
FIG. 4 illustrates a block diagram of an example, non-limiting system including a machine learning classifier that facilitates continual background monitoring of eye health in accordance with one or more embodiments described herein.

FIG. 4 illustrates a block diagram of an example, non-limiting system 400 including a machine learning classifier that can facilitate continual background monitoring of eye health in accordance with one or more embodiments described herein. As shown, the system 400 can, in various embodiments, comprise the same components as the system 300, and can further comprise a machine learning classifier 402.

As explained above, the diagnostic component 118 can leverage the machine learning classifier 402 in order to analyze the images and/or videos received by the sensor component 116 and to estimate, determine, infer, and/or diagnose a health condition of the eyes of the entity 110. In other words, the machine learning classifier 402 can diagnose the eye health of the entity 110 based on the physical characteristics 302 depicted in the images and/or videos of the eyes, face, and/or body of the entity 110 recorded by the camera 106 (e.g., the machine learning classifier 402 can facilitate image recognition, at one point in time or over a period of time, of the images and/or videos recorded by the camera 106). In various embodiments, the machine learning classifier 402 can employ any suitable artificial intelligence, machine learning, and/or deep learning paradigm/architecture that can be trained (e.g., via supervised, unsupervised, and/or reinforcement learning) to classify/label input data (e.g., to identify/classify health conditions/diseases that correspond to the physical characteristics 302 depicted in the images and/or videos recorded by the camera 106). In various aspects, the machine learning classifier 402 can combine (e.g., via any suitable mathematical, statistical, and/or artificial intelligence technique) data from the recorded images and/or videos (e.g., can leverage the physical characteristics 302) to generate features. In various aspects, the machine learning classifier 402 can standardize (e.g., via any suitable mathematical, statistical, and/or artificial intelligence technique) data by applying suitable adjustments.

To facilitate the above-described machine learning aspects of various embodiments of the invention, consider the following discussion of artificial intelligence. Various embodiments of the invention herein can employ artificial intelligence (AI) to facilitate automating one or more features of embodiments of the invention. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of embodiments of the invention, components of embodiments of the invention can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information)) schemes and/or systems (e.g., support vector machines, neural networks, expert systems, Bayesian belief networks, fuzzy logic, data fusion engines) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z1, z2, z3, z4, zn)$, to a confidence that the input belongs to a class, as by $f(z)=confidence(class)$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Figure 5:
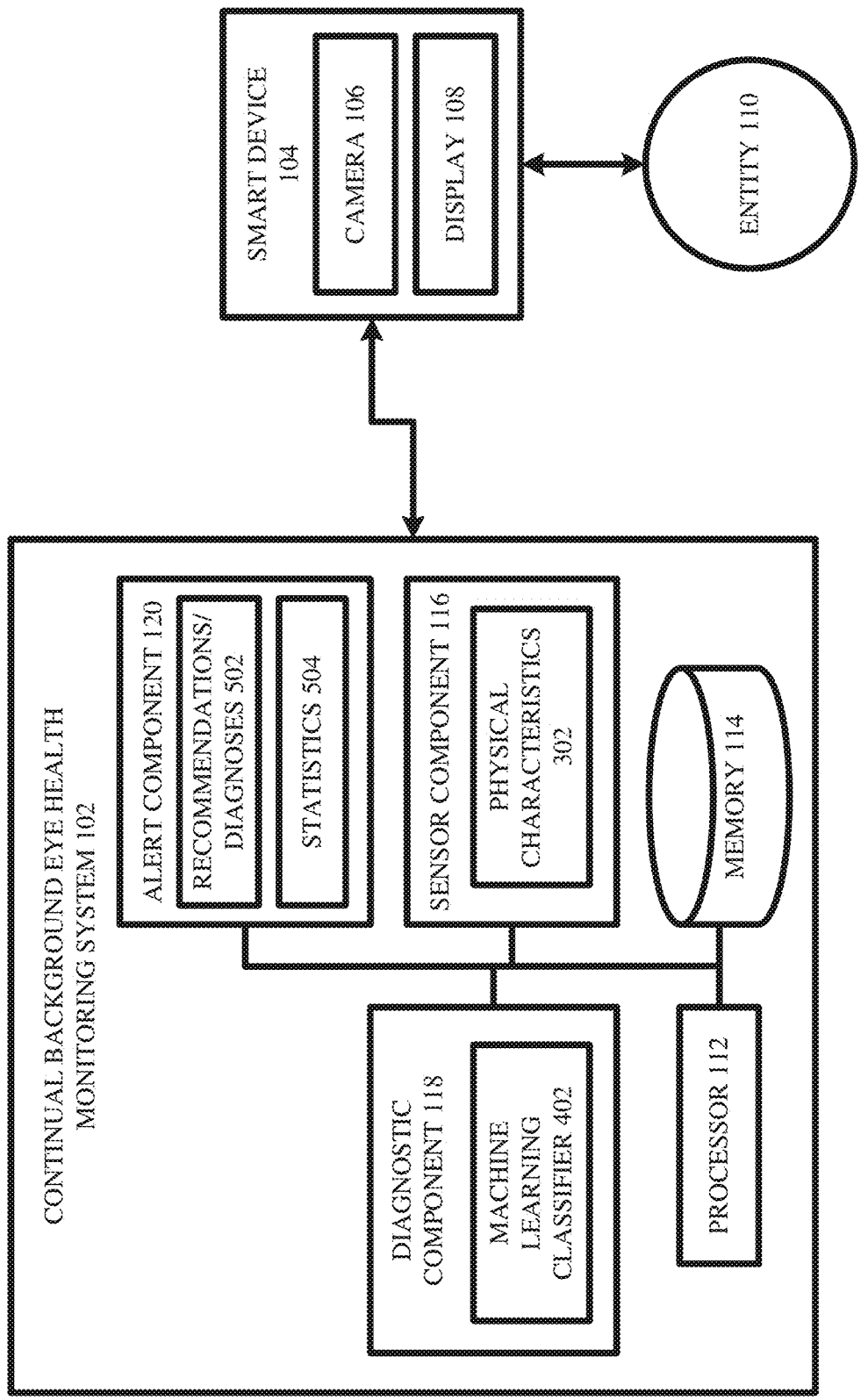
FIG. 5 illustrates a block diagram of an example, non-limiting system including recommendations, diagnoses, and/or statistics that facilitates continual background monitoring of eye health in accordance with one or more embodiments described herein.

FIG. 5 illustrates a block diagram of an example, non-limiting system 500 including recommendations, diagnoses, and/or statistics that can facilitate continual background monitoring of eye health in accordance with one or more embodiments described herein. As shown, the system 500 can, in various aspects, comprise the same components as the system 400, and can further comprise recommendations/diagnoses 502 and statistics 504.

As mentioned above, the alert component 120 can generate an alert that corresponds to the health conditions estimated, inferred, determined, and/or diagnosed by the diagnostic component 118. In various aspects, an alert can include recommendations/diagnoses 502 and/or statistics 504. The recommendations/diagnoses 502 can indicate (e.g., via video, audio, and/or tactile messages delivered and/or presented by the smart device 104) a health condition of the entity 110 and/or suggested treatments and/or actions to take to ameliorate the health condition of the entity 110. For instance, the recommendations/diagnoses 502 can indicate that the entity 110 has red and watery eyes, that red and watery eyes are correlated with excessive eye strain, and that the entity 110 should therefore give their eyes a rest. As another example, the recommendations/diagnoses 502 can indicate that the eyes of the entity 110 have become cloudy, that cloudy eye lenses are correlated with cataracts, and that the entity 110 should therefore seek medical treatment. In various aspects, the statistics 504 can include descriptive statistics related to the eyes of the entity 110 (e.g., blink rate, eye movement, eye wateriness, screen time, squinting rate).

In various aspects, the alert component 120 can utilize any suitable machine learning and/or deep learning technique to generate the recommendations/diagnoses 502 and/or the statistics 504. In various aspects, the machine learning classifier 402 can be trained to generate/predict a health condition of the entity 110 and to generate/predict suggested corrective actions to treat the health condition based on analyzing the physical characteristics 302, and the alert component 120 can prepare and/or format an electronic video, audio, and/or tactile message based on the health condition and suggested corrective actions.

Non-limiting, exemplary alerts generated by the alert component 120 can include the following: "Your eyes are squinting to enhance focus while using the smart device. As observed in many other users, this can be a sign of deteriorating eyesight. Consider consulting a doctor immediately."; "Your eye movement has significantly increased. This can be caused by decrease in visual field. Consider consulting a doctor immediately."; "The blink rate of your eyes has increased significantly as compared to previous behavior. Please consult a doctor."; "Your blink rate has decreased, and the blinks are prolonged. This can be an indicator of tired eyes. You should stop accessing any smart devices and rest your eyes for some time."; "Continuous water running from eyes. Please consult a doctor."; "Your eyes are red. You should consult a doctor."

Figure 6:
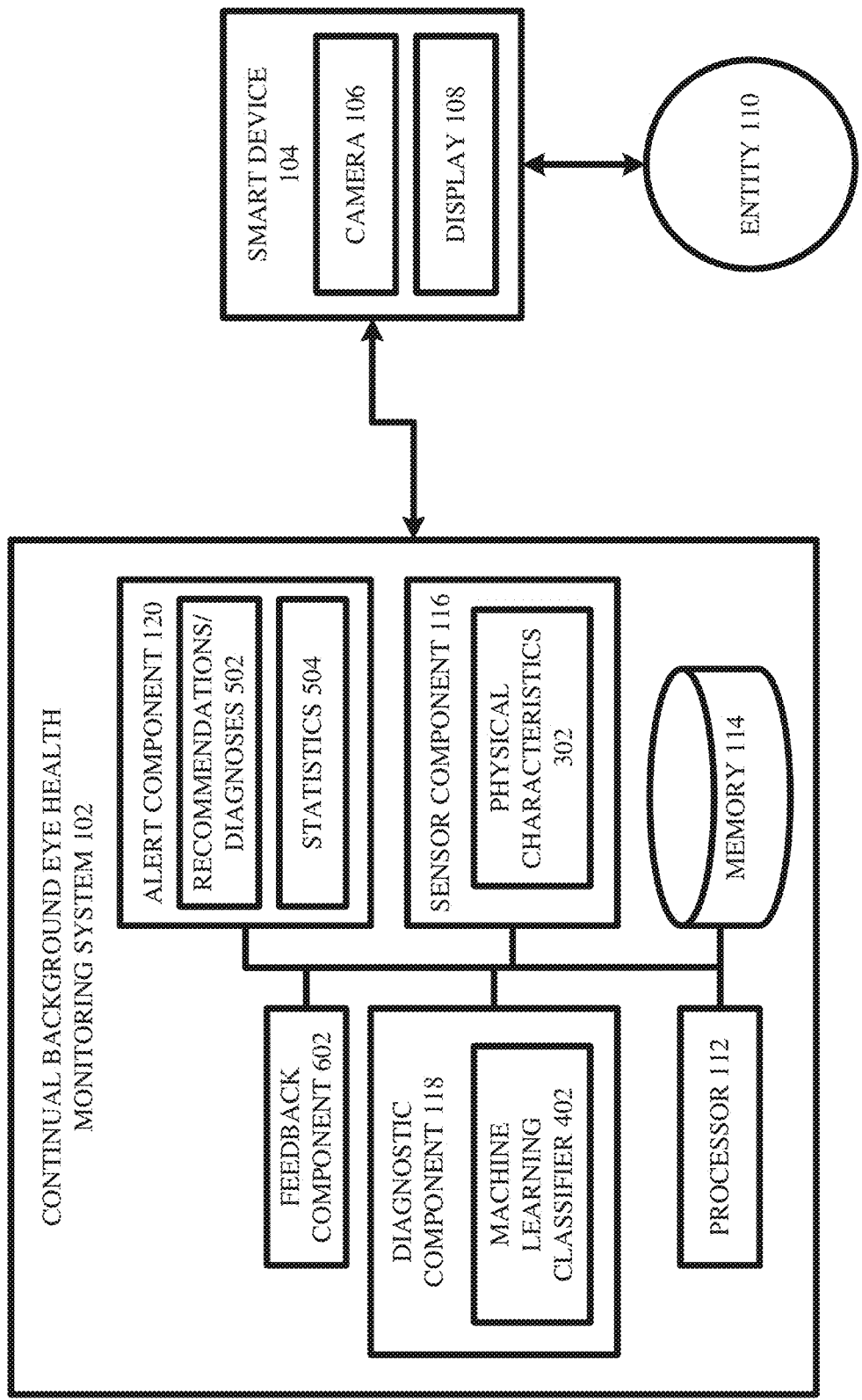
FIG. 6 illustrates a block diagram of an example, non-limiting system including a feedback component that facilitates continual background monitoring of eye health in accordance with one or more embodiments described herein.

FIG. 6 illustrates a block diagram of an example, non-limiting system 600 including a feedback component that can facilitate continual background monitoring of eye health in accordance with one or more embodiments described herein. As shown, the system 600 can, in various cases, comprise the same components as the system 500, and can further comprise a feedback component 602.

In various aspects, the feedback component 602 can receive feedback from the entity 110 characterizing an accuracy and/or a helpfulness of the alert generated and displayed by the alert component 120. In various instances, the feedback component 602 can leverage any suitable interface mechanism of the smart device 104 to receive the feedback from the entity 110 (e.g., the entity 110 can provide feedback by interacting with a touch screen of the smart device 104, a keyboard and/or key pad of the smart device 104, a mouse and/or other pointing device of the smart device 104). In some instances, the feedback component 602 can prompt (e.g., via the display 108) the entity 110 for feedback after the alert component 120 displays (e.g., via the display 108) an alert to the entity 110. In various embodiments, the feedback received by the feedback component 602 can be used to facilitate customization and/or active learning of the machine learning classifier 402. That is, in various cases, the machine learning classifier 402 can be pre-trained to estimate, determine, infer, and/or diagnoses a health condition of the eyes of the entity 110 based on the physical characteristics 302, and the feedback received by the feedback component 602 can be used to update and/or customize parameters of the machine learning classifier 402. For example, suppose the entity 110 is using the smart device, has excessively red and watery eyes, but has not ruptured an ocular blood vessel. Further, suppose that the machine learning classifier 402 diagnoses the entity 110 as having a ruptured ocular blood vessel. In such case, the machine learning classifier 402 has made an incorrect diagnosis. So, in various instances, the feedback component 602 can prompt the entity 110 for feedback, and the entity 110 can provide feedback indicating that he/she does not have a ruptured ocular blood vessel and that he/she instead simply has strained eyes. Based on this feedback, the feedback component 602 and/or the diagnostic component 118 can update (e.g., via backpropagation and/or any other suitable updating technique) the parameters (e.g., weights and/or biases) of the machine learning classifier 402. In this way, the feedback component 602 can facilitate active learning of the machine learning classifier 402 (e.g., can help the machine learning classifier 402 learn from its mistakes).

In some embodiments, the feedback component 602 can also prompt the entity 110 for alert preferences (e.g., can ask how the entity 110 would like to receive alerts, such as visually, audibly, and/or tactilely; can ask how many alerts the entity 110 would like to receive per time interval; can ask what types of diagnoses, recommendations, and/or statistics the entity 110 would like to receive in an alert). Thus, in various aspects, the feedback component 602 can receive information from the entity 110 so that the alert component 120 can appropriately customize and/or filter alerts according to the preferences of the entity 110.

Figure 7:
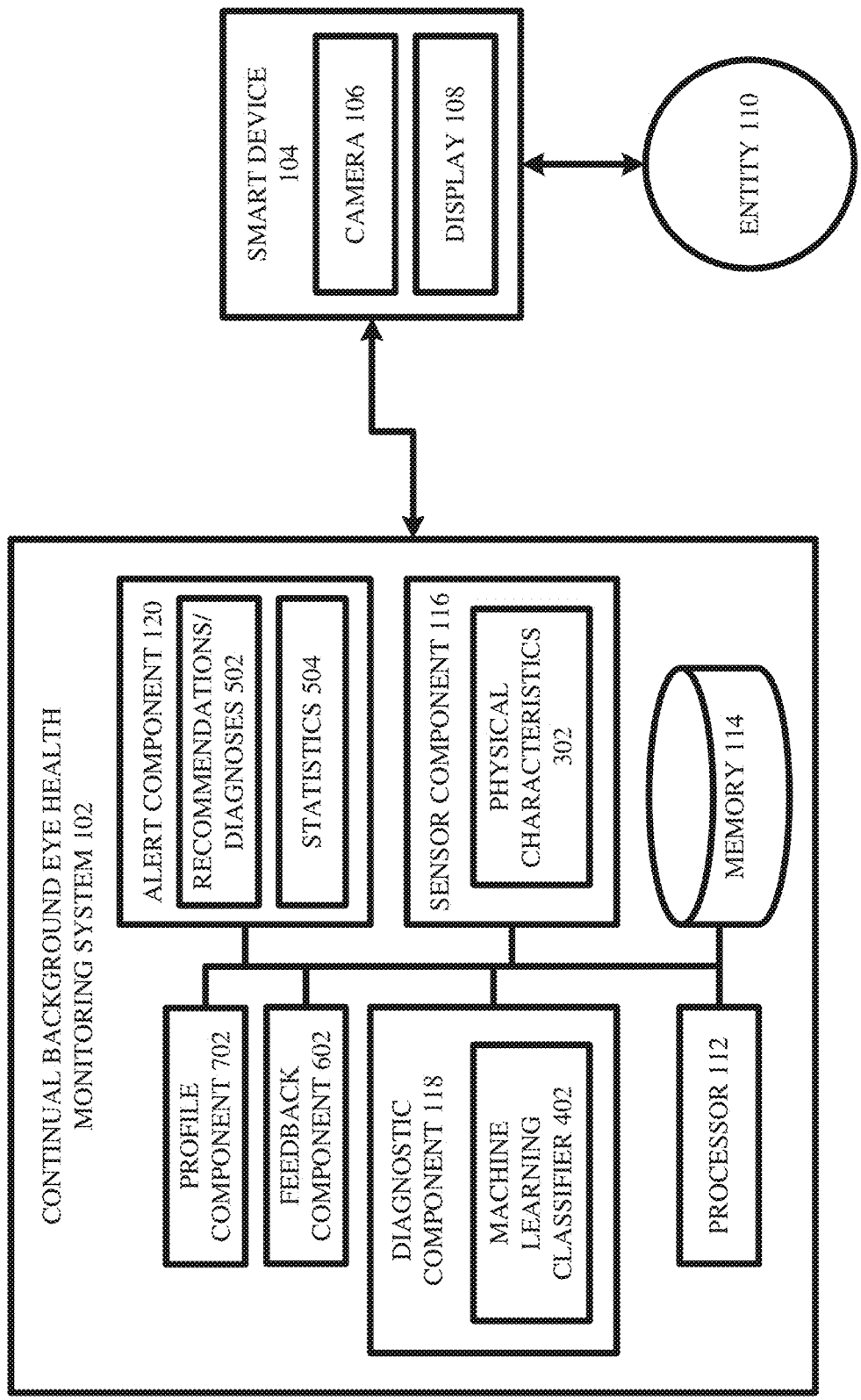
FIG. 7 illustrates a block diagram of an example, non-limiting system including a profile component that facilitates continual background monitoring of eye health in accordance with one or more embodiments described herein.

FIG. 7 illustrates a block diagram of an example, non-limiting system 700 including a profile component that can facilitate continual background monitoring of eye health in accordance with one or more embodiments described herein. As shown, the system 700 can, in various aspects, comprise the same components as the system 600, and can further comprise a profile component 702.

In various embodiments, the profile component 702 can generate an eye health profile of the entity 110 and can share the eye health profile with another smart device (not shown) of the entity 110. In various aspects, the eye health profile can be any suitable electronic file and/or document that stores the physical characteristics 302 received by the sensor component 116 (e.g., stores the recorded images and/or videos of the eyes, face, and/or body of the entity 110), stores the classifications/labels outputted by the diagnostic component 118 (e.g., stores the determinations, inferences, and/or diagnoses produced by the machine learning classifier 402), stores the alerts generated and/or displayed by the alert component 120, and/or stores the feedback received by the feedback component 602. In various aspects, the eye health profile can be considered as a comprehensive eye health history of the entity 110. Moreover, the eye health profile can be shared across multiple smart devices of the entity 110. For example, suppose that the entity 110 interacts with a smart phone for a first time period, a smart television for a second time period, and a laptop computer for a third time period. The smart phone can continually monitor in a processing background the eye health of the entity 110 during the first time period and can update the eye health profile of the entity 110 accordingly. The smart television can continually monitor in a processing background the eye health of the entity 110 during the second time period and can update the eye health profile of the entity 110 accordingly. Since the second time period succeeds the first time period, the smart television can have access to and/or can base its diagnoses on pertinent information regarding the eye health of the entity 110 that occurred and/or was recorded during the first time period (e.g., the smart television can base its diagnoses in part on eye health events that occurred when the entity 110 was not using the smart television). Similarly, the laptop computer can continually monitor in a processing background the eye health of the entity 110 during the third time period and can update the eye health profile of the entity 110 accordingly. Since the third time period succeeds both the first and second time periods, the laptop computer can have access to and/or can base its diagnoses on pertinent information regarding the eye health of the entity 110 that occurred and/or was recorded during the first and/or second time periods (e.g., the laptop computer can base its diagnoses in part on eye health events that occurred when the entity 110 was not using the laptop computer). In this way, the eye health of the entity 110 can be tracked across multiple smart devices, and a comprehensive eye health history corresponding to the entity 110 can be tracked. This can provide deeper, richer, smoother, and more accurate data regarding the eye health of the entity 110, as compared to traditional eye exams performed once every several months.

In various embodiments, more than one entity can use the smart device 104. In such cases, the profile component 702 can employ facial recognition in order to identify the particular entity that is using the smart device 104 at any given time. Once the particular entity currently using the smart device is identified, a corresponding eye health profile can be accessed and/or updated. In this way, the smart device 104 can track the eye health histories (e.g., physical characteristics, diagnoses, alerts, feedback) of multiple entities at once. Thus, various embodiments of the invention can provide customized continual background eye health monitoring based on the identity of the entity 110.

Figure 8:
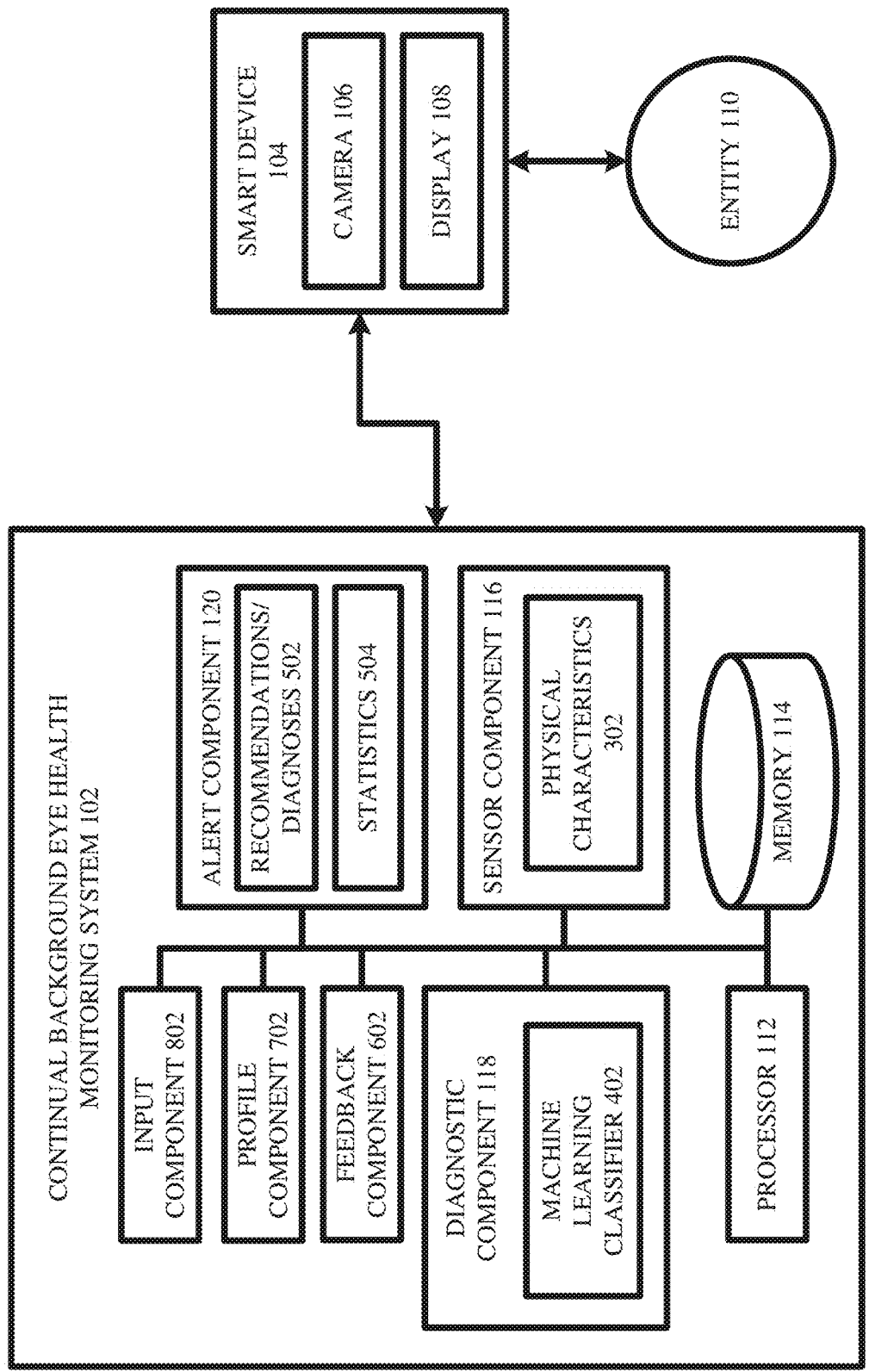
FIG. 8 illustrates a block diagram of an example, non-limiting system including an input component that facilitates continual background monitoring of eye health in accordance with one or more embodiments described herein.

FIG. 8 illustrates a block diagram of an example, non-limiting system 800 including an input component that can facilitate continual background monitoring of eye health in accordance with one or more embodiments described herein. As shown, the system 800 can, in various embodiments, comprise the same components as the system 700, and can further comprise an input component 802.

In various embodiments, the input component 802 can receive input information from the entity 110. In various aspects, the machine learning classifier 402 can be trained to output its diagnoses, estimations, determinations, and/or inferences based at least in part on the input information received by the input component 802. In various aspects, the input information can comprise at least one of diet of the entity 110, body weight and/or body mass index of the entity 110, age of the entity 110, pre-existing medical conditions and/or medical history of the entity 110, current medicines and/or medications of the entity 110, and/or any other suitable demographic information regarding the entity 110. In various aspects, the entity 110 can interact with any suitable interface device of the smart device 104 to provide the input information. In various aspects, the input component 802 can receive the input information from any suitable electronic file and/or database which can be electronically accessed by the input component 802. For example, in some cases, the smart device 104 can have a health/exercise app which can be accessed by the input component 802 to retrieve the input information. In various aspects, the machine learning classifier 402 can standardize and/or normalize the physical characteristics 302 based on the input information received by the input component 802 and/or based on ambient conditions of the smart device 104 (e.g., lighting and/or temperature).

Figure 9:
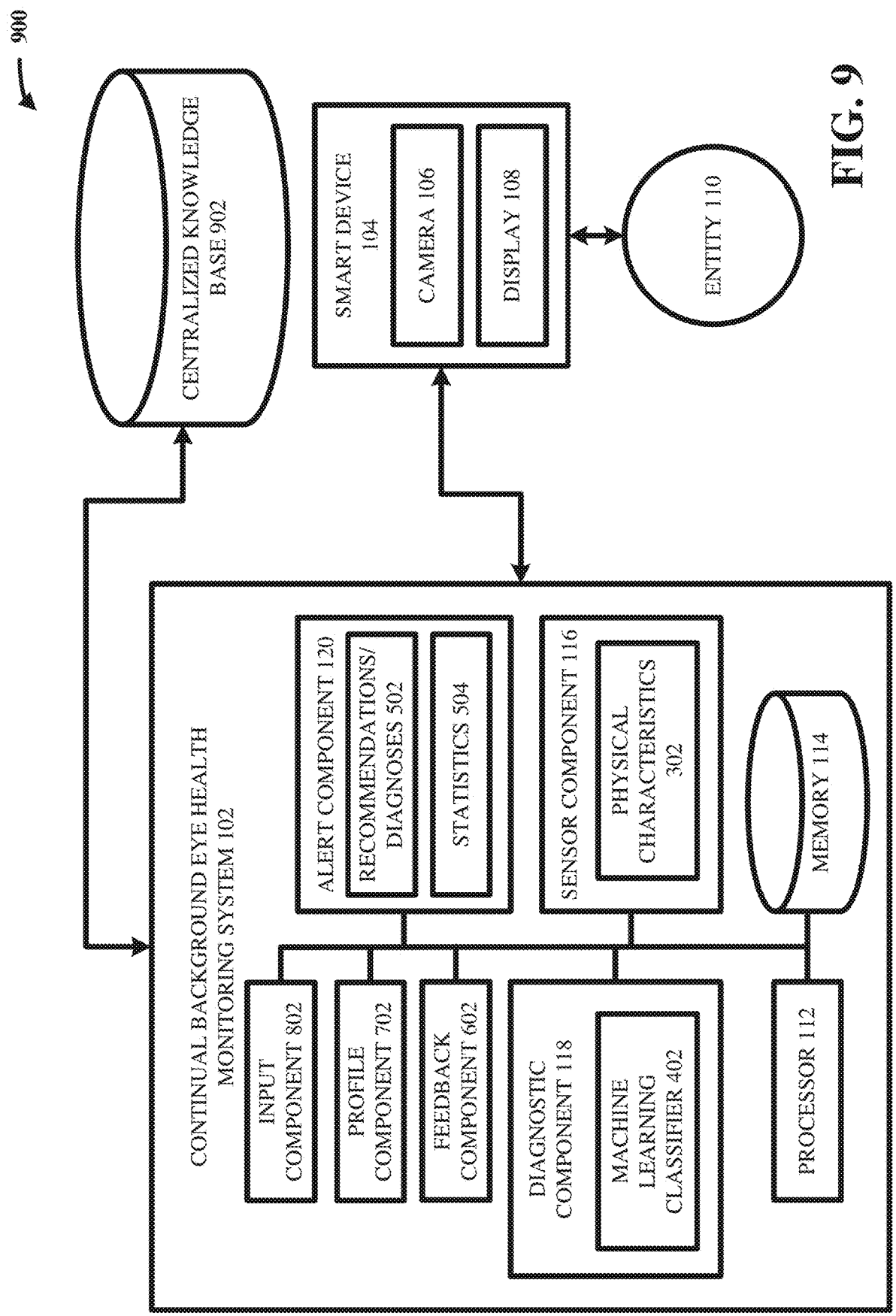
FIG. 9 illustrates a block diagram of an example, non-limiting system including a centralized knowledge base that facilitates continual background monitoring of eye health in accordance with one or more embodiments described herein.

FIG. 9 illustrates a block diagram of an example, non-limiting system 900 including a centralized knowledge base that can facilitate continual background monitoring of eye health in accordance with one or more embodiments described herein. As shown, the system 900 can, in various aspects, comprise the same components as the system 800, and can further comprise a centralized knowledge base 902.

In various embodiments, the centralized knowledge base 902 can be any suitable database that receives and/or stores feedback from multiple entities across multiple smart devices. In various aspects, the continual background eye health monitoring system 102 can be communicatively coupled to the centralized knowledge base 902 via any suitable wired and/or wireless electronic connection. As explained above, the feedback component 602 can facilitate active learning and/or updating of the machine learning classifier 402 by receiving feedback from the entity 110. Similarly, the centralized knowledge base 902 can facilitate active learning and/or updating of the machine learning classifier 402 by receiving feedback from multiple other entities interacting with multiple other smart devices. For example, suppose that entity A has a smart phone that can facilitate continual background monitoring of eye health, entity B has a smart television that can facilitate continual background monitoring of eye health, and entity C has a smart tablet that can facilitate continual background monitoring of eye health. Moreover, suppose that the smart phone, the smart television, and the smart tablet are all communicatively coupled to the centralized knowledge base 902. Furthermore, suppose that the smart phone has not mistakenly classified/labeled a health condition of the eyes of entity A, while the smart television has mistakenly classified/labeled a health condition of the eyes of entity B and the smart tablet has mistakenly classified/labeled a health condition of the eyes of entity C. In various aspects, entity B can provide feedback to the smart television (e.g., via a feedback component of the smart television) and entity C can provide feedback to the smart tablet (e.g., via a feedback component of the smart tablet). Accordingly, the smart television can update its machine learning classifier based on the feedback from entity B, and the smart tablet can update its machine learning classifier based on the feedback from entity C. In various aspects, the feedback from entity B can be transmitted to and/or stored in the centralized knowledge base 902. Similarly, the feedback from entity C can be transmitted to and/or stored in the centralized knowledge base 902. In various instances, since the smart phone is communicatively coupled to the centralized knowledge base 902, the smart phone can have access to the feedback of entity B and the feedback of entity C. Thus, in various cases, the smart phone of entity A can update its machine learning classifier based on the feedback from entity B and the feedback from entity C. In other words, the smart phone can learn from the mistakes of the smart television and the smart tablet. In this way, the centralized knowledge base 902 can facilitate the smart device 104 learning from classification/labeling errors of other, separate smart devices used by other, separate entities.

In various aspects, thousands of different entities can interact with thousands of smart devices. By collecting/receiving feedback from such numerous entities, embodiments of the invention can exhibit significantly improved diagnostic classification/labeling capabilities and significantly improved recommendation generation.

In various cases, the centralized knowledge base 902 can facilitate a forward feedback learning technique that compares the classification/label generated by the diagnostic component 118, the metrics (e.g., physical characteristics 302) of each one of the detection methods that contributed to the classification/label, and the recommended mitigation solutions generated by the alert component 120 to a database of thousands of other entities and/or also to the personal history of the entity 110.

Figure 10:
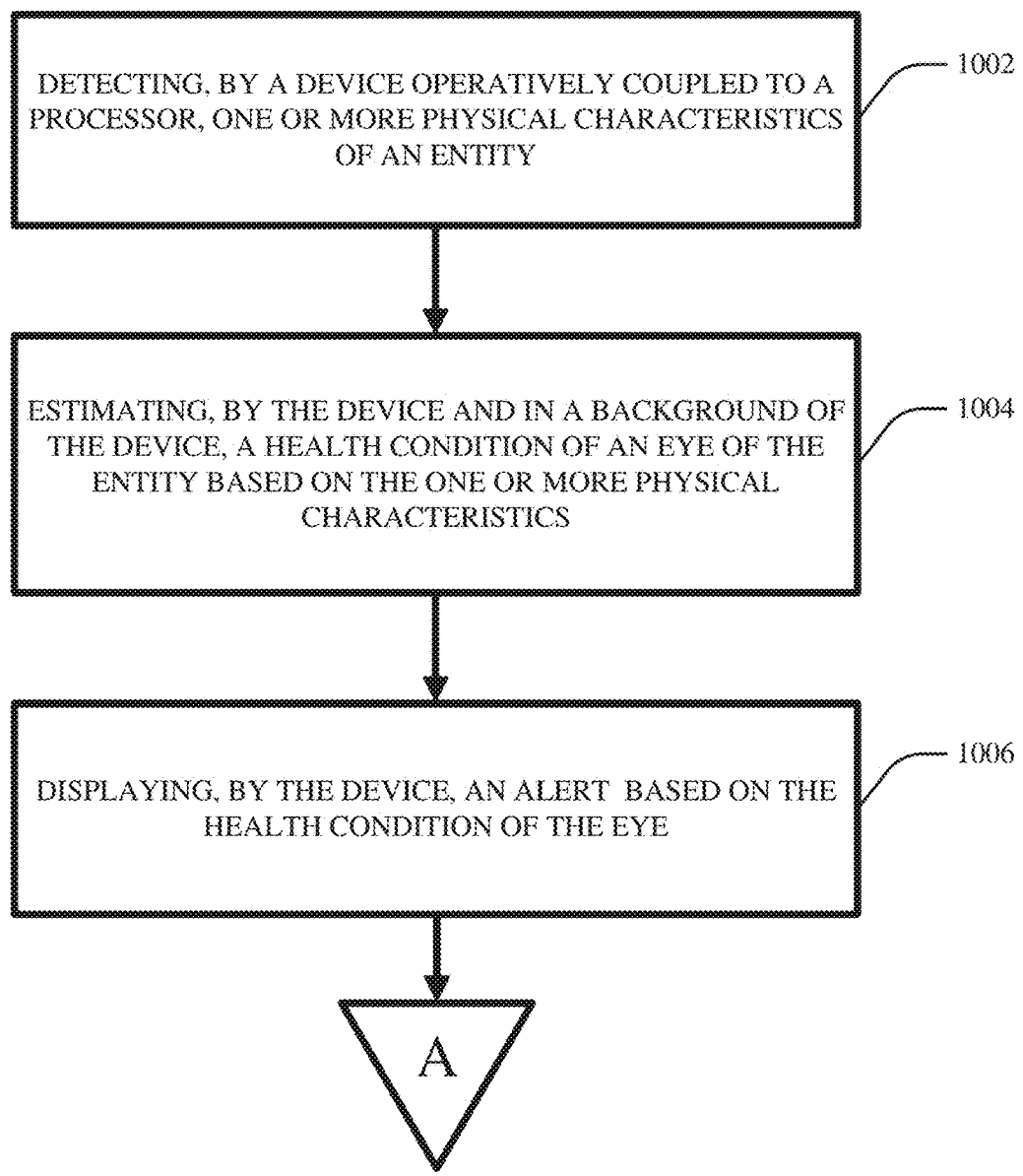
FIG. 10 illustrates a flow diagram of an example, non-limiting computer-implemented method that facilitates continual background monitoring of eye health in accordance with one or more embodiments described herein.

FIG. 10 illustrates a flow diagram of an example, non-limiting computer-implemented method 1000 that can facilitate continual background monitoring of eye health in accordance with one or more embodiments described herein.

In various embodiments, act 1002 can include detecting, by a device operatively coupled to a processor (e.g., 116 and 104), one or more physical characteristics (e.g., 302) of an entity (e.g., 110).

In various aspects, act 1004 can include continually estimating, by the device and in a background of the device (e.g., 118, 402, and 104), a health condition of an eye of the entity based on the one or more physical characteristics.

In various instances, act 1006 can include displaying, by the device (e.g., 120), an alert (e.g., 502 and/or 504) based on the health condition of the eye.

Figure 11:
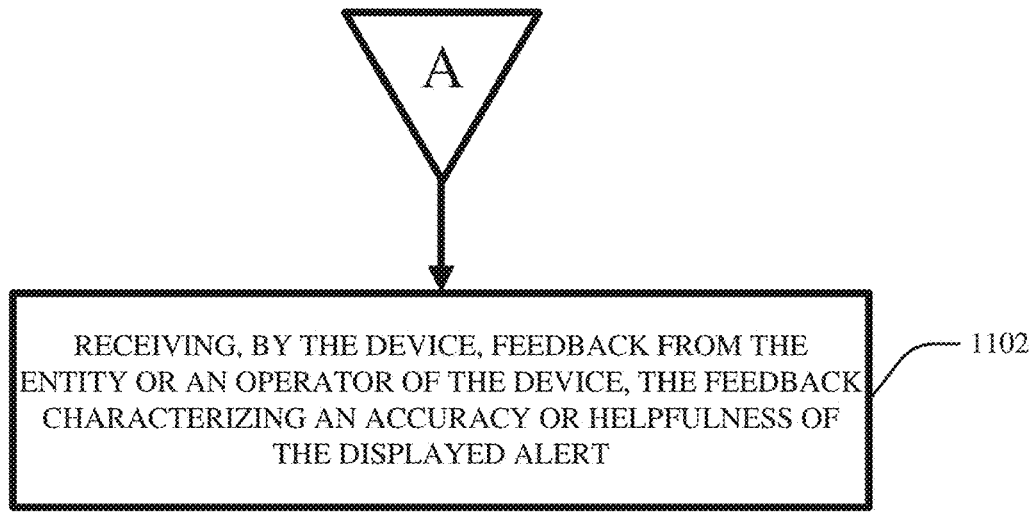
FIG. 11 illustrates a flow diagram of an example, non-limiting computer-implemented method including receiving feedback that facilitates continual background monitoring of eye health in accordance with one or more embodiments described herein.

FIG. 11 illustrates a flow diagram of an example, non-limiting computer-implemented method 1100 including receiving feedback that can facilitate continual background monitoring of eye health in accordance with one or more embodiments described herein. As shown, the computer-implemented method 1100 can, in various aspects, comprise the same acts as the computer-implemented method 1000, and can further comprise act 1102.

In various aspects, act 1102 can include receiving, by the device (e.g., 602), feedback from the entity or an operator of the device, the feedback characterizing an accuracy or helpfulness of the displayed alert.

Figure 12:
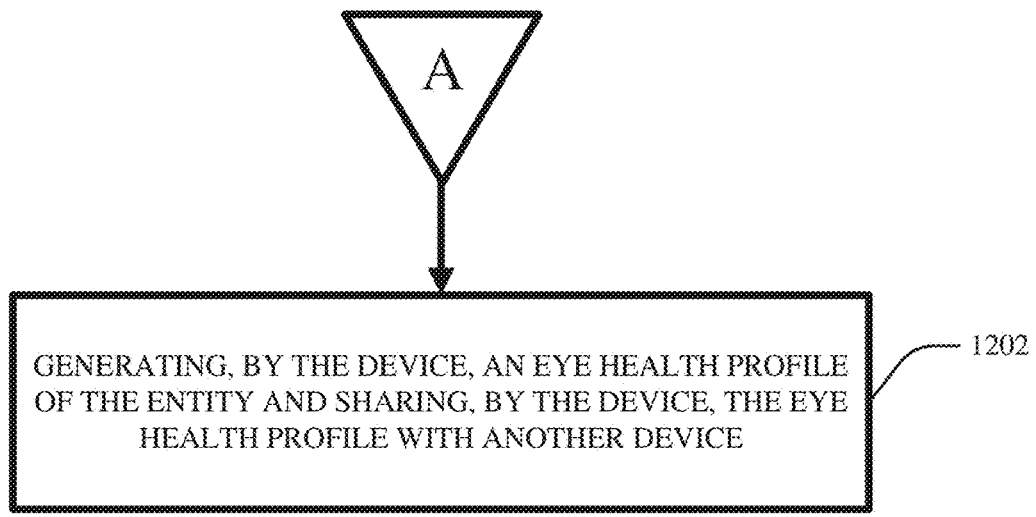
FIG. 12 illustrates a flow diagram of an example, non-limiting computer-implemented method including generating an eye health profile that facilitates continual background monitoring of eye health in accordance with one or more embodiments described herein.

FIG. 12 illustrates a flow diagram of an example, non-limiting computer-implemented method 1200 including generating an eye health profile that can facilitate continual background monitoring of eye health in accordance with one or more embodiments described herein. As shown, the computer-implemented method 1200 can, in various aspects, comprise the same acts as the computer-implemented method 1000, and can further comprise act 1202.

In various cases, act 1202 can include generating, by the device (e.g., 702), an eye health profile of the entity and sharing, by the device (e.g., 702), the eye health profile with another device.

Figure 13:
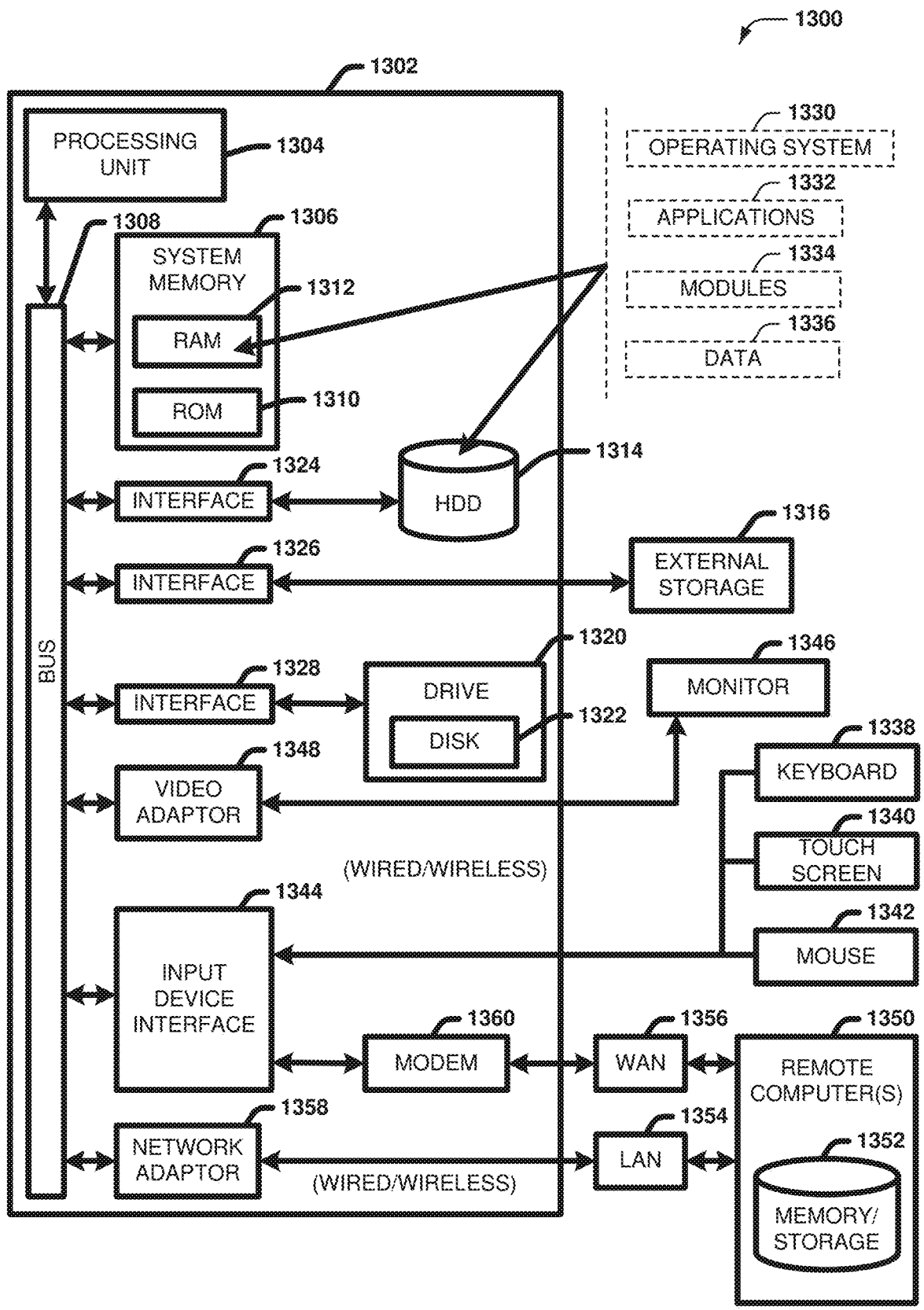
FIG. 13 illustrates a block diagram of an example, non-limiting operating environment in which one or more embodiments described herein can be facilitated.

In order to provide additional context for various embodiments described herein, FIG. 13 and the following discussion are intended to provide a general description of a suitable computing environment 1300 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 13, the example environment 1300 for implementing various embodiments of the aspects described herein includes a computer 1302, the computer 1302 including a processing unit 1304, a system memory 1306 and a system bus 1308. The system bus 1308 couples system components including, but not limited to, the system memory 1306 to the processing unit 1304. The processing unit 1304 can be any of various commercially available processors. Dual microprocessors and other multi-processor architectures can also be employed as the processing unit 1304.

The system bus 1308 can be any of several types of bus structure that can further interconnect to a memory bus (with or without a memory controller), a peripheral bus, and a local bus using any of a variety of commercially available bus architectures. The system memory 1306 includes ROM 1310 and RAM 1312. A basic input/output system (BIOS) can be stored in a non-volatile memory such as ROM, erasable programmable read only memory (EPROM), EEPROM, which BIOS contains the basic routines that help to transfer information between elements within the computer 1302, such as during startup. The RAM 1312 can also include a high-speed RAM such as static RAM for caching data.

The computer 1302 further includes an internal hard disk drive (HDD) 1314 (e.g., EIDE, SATA), one or more external storage devices 1316 (e.g., a magnetic floppy disk drive (FDD) 1316, a memory stick or flash drive reader, a memory card reader, etc.) and a drive 1320, e.g., such as a solid state drive, an optical disk drive, which can read or write from a disk 1322, such as a CD-ROM disc, a DVD, a BD, etc. Alternatively, where a solid state drive is involved, disk 1322 would not be included, unless separate. While the internal HDD 1314 is illustrated as located within the computer 1302, the internal HDD 1314 can also be configured for external use in a suitable chassis (not shown). Additionally, while not shown in environment 1300, a solid state drive (SSD) could be used in addition to, or in place of, an HDD 1314. The HDD 1314, external storage device(s) 1316 and drive 1320 can be connected to the system bus 1308 by an HDD interface 1324, an external storage interface 1326 and a drive interface 1328, respectively. The interface 1324 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1302, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1312, including an operating system 1330, one or more application programs 1332, other program modules 1334 and program data 1336. All or portions of the operating system, applications, modules, and/or data can also be cached in the RAM 1312. The systems and methods described herein can be implemented utilizing various commercially available operating systems or combinations of operating systems.

Computer 1302 can optionally comprise emulation technologies. For example, a hypervisor (not shown) or other intermediary can emulate a hardware environment for operating system 1330, and the emulated hardware can optionally be different from the hardware illustrated in FIG. 13. In such an embodiment, operating system 1330 can comprise one virtual machine (VM) of multiple VMs hosted at computer 1302. Furthermore, operating system 1330 can provide runtime environments, such as the Java runtime environment or the .NET framework, for applications 1332. Runtime environments are consistent execution environments that allow applications 1332 to run on any operating system that includes the runtime environment. Similarly, operating system 1330 can support containers, and applications 1332 can be in the form of containers, which are lightweight, standalone, executable packages of software that include, e.g., code, runtime, system tools, system libraries and settings for an application.

Further, computer 1302 can be enable with a security module, such as a trusted processing module (TPM). For instance with a TPM, boot components hash next in time boot components, and wait for a match of results to secured values, before loading a next boot component. This process can take place at any layer in the code execution stack of computer 1302, e.g., applied at the application execution level or at the operating system (OS) kernel level, thereby enabling security at any level of code execution.

A user can enter commands and information into the computer 1302 through one or more wired/wireless input devices, e.g., a keyboard 1338, a touch screen 1340, and a pointing device, such as a mouse 1342. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1304 through an input device interface 1344 that can be coupled to the system bus 1308, but can be connected by other interfaces, such as a parallel port, an IEEE 1394 serial port, a game port, a USB port, an IR interface, a BLUETOOTH® interface, etc.

A monitor 1346 or other type of display device can be also connected to the system bus 1308 via an interface, such as a video adapter 1348. In addition to the monitor 1346, a computer typically includes other peripheral output devices (not shown), such as speakers, printers, etc.

The computer 1302 can operate in a networked environment using logical connections via wired and/or wireless communications to one or more remote computers, such as a remote computer(s) 1350. The remote computer(s) 1350 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1352 is illustrated. The logical connections depicted include wired/wireless connectivity to a local area network (LAN) 1354 and/or larger networks, e.g., a wide area network (WAN) 1356. Such LAN and WAN networking environments are commonplace in offices and companies, and facilitate enterprise-wide computer networks, such as intranets, all of which can connect to a global communications network, e.g., the Internet.

When used in a LAN networking environment, the computer 1302 can be connected to the local network 1354 through a wired and/or wireless communication network interface or adapter 1358. The adapter 1358 can facilitate wired or wireless communication to the LAN 1354, which can also include a wireless access point (AP) disposed thereon for communicating with the adapter 1358 in a wireless mode.

When used in a WAN networking environment, the computer 1302 can include a modem 1360 or can be connected to a communications server on the WAN 1356 via other means for establishing communications over the WAN 1356, such as by way of the Internet. The modem 1360, which can be internal or external and a wired or wireless device, can be connected to the system bus 1308 via the input device interface 1344. In a networked environment, program modules depicted relative to the computer 1302 or portions thereof, can be stored in the remote memory/storage device 1352. It will be appreciated that the network connections shown are example and other means of establishing a communications link between the computers can be used.

When used in either a LAN or WAN networking environment, the computer 1302 can access cloud storage systems or other network-based storage systems in addition to, or in place of, external storage devices 1316 as described above, such as but not limited to a network virtual machine providing one or more aspects of storage or processing of information. Generally, a connection between the computer 1302 and a cloud storage system can be established over a LAN 1354 or WAN 1356 e.g., by the adapter 1358 or modem 1360, respectively. Upon connecting the computer 1302 to an associated cloud storage system, the external storage interface 1326 can, with the aid of the adapter 1358 and/or modem 1360, manage storage provided by the cloud storage system as it would other types of external storage. For instance, the external storage interface 1326 can be configured to provide access to cloud storage sources as if those sources were physically connected to the computer 1302.

The computer 1302 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a network or simply an ad hoc communication between at least two devices.

Figure 14:
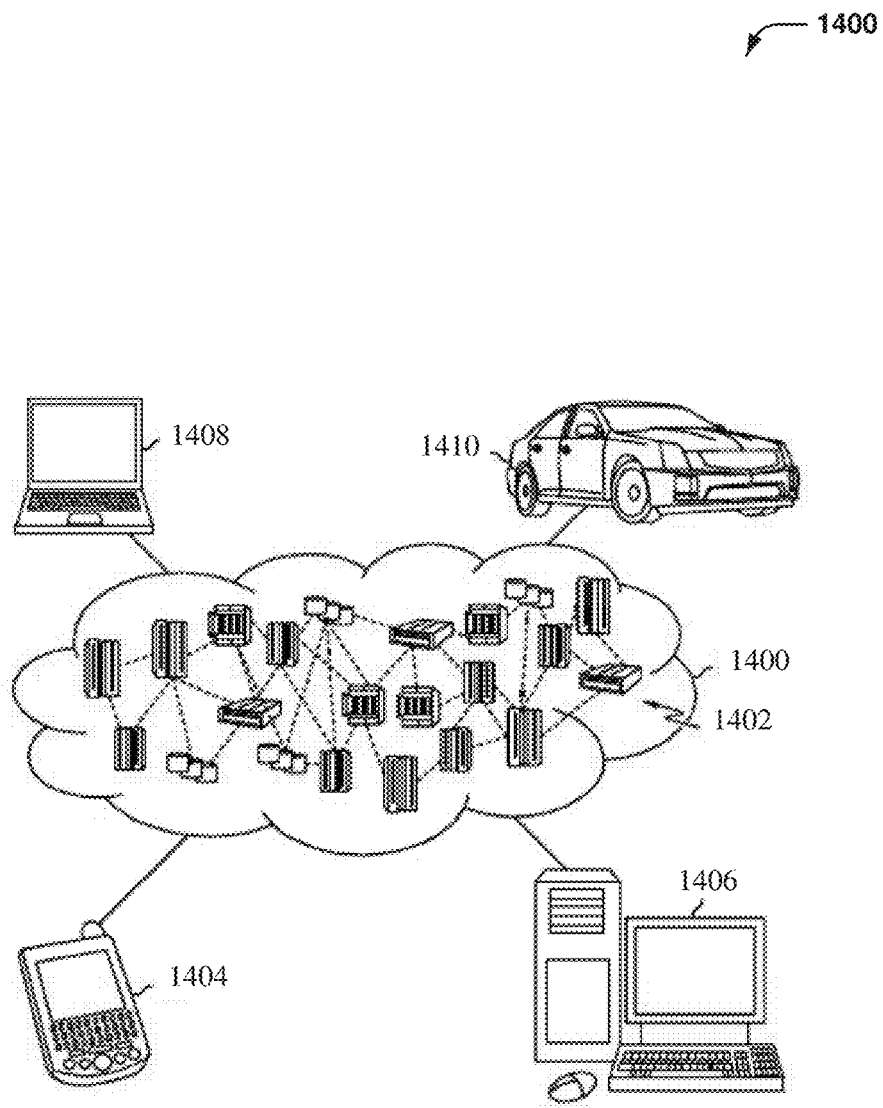
FIG. 14 illustrates an example, non-limiting cloud computing environment in accordance with one or more embodiments described herein.

Referring now to FIG. 14, illustrative cloud computing environment 1400 is depicted. As shown, cloud computing environment 1400 includes one or more cloud computing nodes 1402 with which local computing devices used by cloud consumers, such as, for example, personal digital assistant (PDA) or cellular telephone 1404, desktop computer 1406, laptop computer 1408, and/or automobile computer system 1410 may communicate. Nodes 1402 may communicate with one another. They may be grouped (not shown) physically or virtually, in one or more networks, such as Private, Community, Public, or Hybrid clouds as described hereinabove, or a combination thereof. This allows cloud computing environment 1400 to offer infrastructure, platforms and/or software as services for which a cloud consumer does not need to maintain resources on a local computing device. It is understood that the types of computing devices 1404-1410 shown in FIG. 14 are intended to be illustrative only and that computing nodes 1402 and cloud computing environment 1400 can communicate with any type of computerized device over any type of network and/or network addressable connection (e.g., using a web browser).

Figure 15:
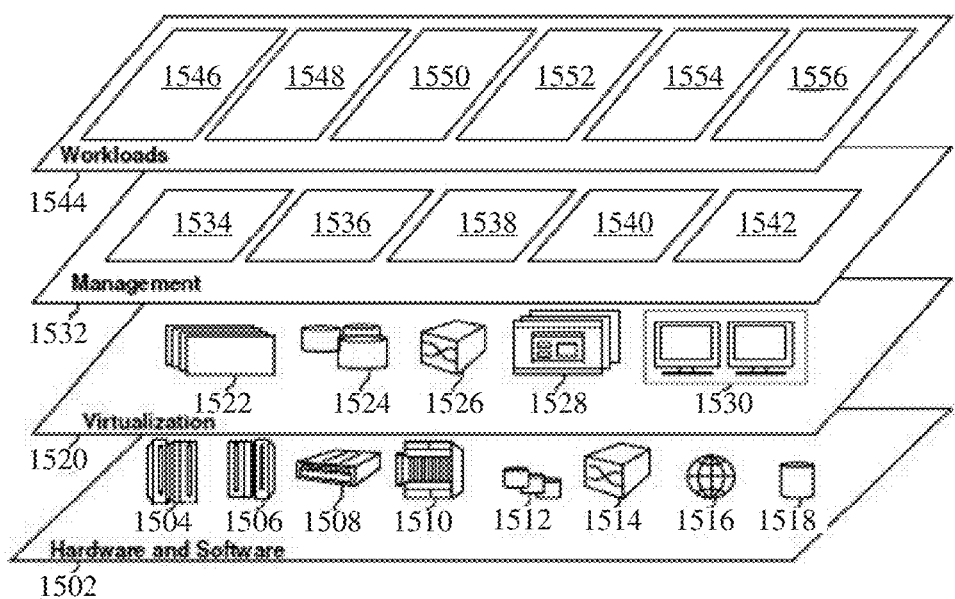
FIG. 15 illustrates example, non-limiting abstraction model layers in accordance with one or more embodiments described herein.

Referring now to FIG. 15, a set of functional abstraction layers provided by cloud computing environment 1400 (FIG. 14) is shown. Repetitive description of like elements employed in other embodiments described herein is omitted for sake of brevity. It should be understood in advance that the components, layers, and functions shown in FIG. 15 are intended to be illustrative only and embodiments of the invention are not limited thereto. As depicted, the following layers and corresponding functions are provided.

Hardware and software layer 1502 includes hardware and software components. Examples of hardware components include: mainframes 1504; RISC (Reduced Instruction Set Computer) architecture based servers 1506; servers 1508; blade servers 1510; storage devices 1512; and networks and networking components 1514. In some embodiments, software components include network application server software 1516 and database software 1518.

Virtualization layer 1520 provides an abstraction layer from which the following examples of virtual entities may be provided: virtual servers 1522; virtual storage 1524; virtual networks 1526, including virtual private networks; virtual applications and operating systems 1528; and virtual clients 1530.

In one example, management layer 1532 may provide the functions described below. Resource provisioning 1534 provides dynamic procurement of computing resources and other resources that are utilized to perform tasks within the cloud computing environment. Metering and Pricing 1536 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1538 provides access to the cloud computing environment for consumers and system administrators. Service level management 1540 provides cloud computing resource allocation and management such that required service levels are met. Service Level Agreement (SLA) planning and fulfillment 1542 provide pre-arrangement for, and procurement of, cloud computing resources for which a future requirement is anticipated in accordance with an SLA.

Workloads layer 1544 provides examples of functionality for which the cloud computing environment may be utilized. Examples of workloads and functions which may be provided from this layer include: mapping and navigation 1546; software development and lifecycle management 1548; virtual classroom education delivery 1550; data analytics processing 1552; transaction processing 1554; and differentially private federated learning processing 1556. Various embodiments of the present invention can utilize the cloud computing environment described with reference to FIGS. 14 and 15 to execute one or more differentially private federated learning process in accordance with various embodiments described herein.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adaptor card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory storing computer-executable components; and
a processor that executes the computer-executable components stored in the memory, the computer-executable components comprising:
a diagnostic component that:
trains, using training data comprising images of respective physical characteristics of entities, a neural network to determine health conditions of eyes of the entities;
monitors, in real-time using respective sensors of different devices, while an entity performs activities on the different devices, physical characteristics of the entity associated with determining possible health conditions of an eye of the entity, wherein the activities are unrelated to determining the possible health conditions of the eye, and wherein the monitoring occurs in a background of the different devices without interrupting the entity from performing the activities, and wherein the physical characteristics of the entity comprise respective viewing angles of the entity associated with sizes of images displayed on the different devices;
determines, using the neural network, a health condition of the eye of the entity from the possible health conditions based on the physical characteristics;
receives, from the entity, feedback regarding an accuracy of the determined health condition of the eye of the entity; and
retrains the neural network based on the feedback.

2. The system of claim 1, wherein the computer-executable components further comprise:
an alert component that displays on a screen an alert based on the health condition of the eye.

3. The system of claim 2, wherein the
feedback further indicates a helpfulness of the displayed alert.

4. The system of claim 1, wherein the diagnostic component instantiates a session with a medical professional that enables the medical professional to remotely control a device of the different devices to monitor the health condition of the eye of the entity.

5. The system of claim 1, wherein the diagnostic component continually monitors the health condition of the eye while the entity performs the activities on the different devices.

6. The system of claim 1, wherein at least one of the respective sensors comprises a camera, and wherein the physical characteristics further comprise at least one of eye movement, blink rate, pupil contraction, pupil dilation, squinting, wateriness of the eye, redness of the eye, facial expression of the entity, posture of the entity, or distance between the eye and the camera.

7. The system of claim 6, wherein the computer-executable components further comprise:
an input component that receives input comprising at least one of a diet of the entity, a body weight of the entity, or a medical condition of the entity, wherein the diagnostic component determines the health condition of the eye based further on the input.

8. The system of claim 1, wherein the computer-executable components further comprise:
a profile component that generates an eye health profile of the entity, and tracks changes to the physical characteristics over time in the eye health profile.

9. A computer-implemented method, comprising:
training, by a system operatively coupled to a processor, using training data comprising images of respective physical characteristics of entities, a neural network to determine health conditions of eyes of the entities;
monitoring, by the system, in real-time using respective sensors of different devices, while an entity performs activities on the different devices, physical characteristics of the entity associated with determining possible health conditions of an eye of the entity, wherein the activities are unrelated to determining the possible health conditions of the eye, and wherein the monitoring occurs in a background of the different devices without interrupting the entity from performing the activities, and wherein the physical characteristics of the entity comprise respective viewing angles of the entity associated with sizes of images displayed on the different devices;
determining, by the system, using the neural network, a health condition of the eye of the entity from the possible health conditions based on the physical characteristics;
receiving, by the system, from the entity, feedback regarding an accuracy of the determined health condition of the eye of the entity; and
retrains, by the system, the neural network based on the feedback.

10. The computer-implemented method of claim 9, further comprising:
displaying, by the system, an alert based on the health condition of the eye.

11. The computer-implemented method of claim 10, wherein the feedback further indicates a helpfulness of the displayed alert.

12. The computer-implemented method of claim 9, instantiating, by the system, a session with a medical professional that enables the medical professional to remotely control a device of the different devices to monitor the health condition of the eye of the entity.

13. The computer-implemented method of claim 9, further comprising monitoring, by the system, the health condition of the eye periodically while the entity performs the activities on the different devices.

14. The computer-implemented method of claim 9, wherein at least one of the respective sensors comprises a camera, and wherein the physical characteristics comprise at least one of eye movement, blink rate, pupil contraction, pupil dilation, squinting, wateriness of the eye, redness of the eye, facial expression of the entity, posture of the entity, or distance between the eye and the camera.

15. The computer-implemented method of claim 14, further comprising:
receiving, by the system, input comprising at least one of a diet of the entity, a body weight of the entity, or a medical condition of the entity, wherein the determining the health condition of the eye is based at least in part on the input.

16. The computer-implemented method of claim 9, further comprising:

generating, by the system, an eye health profile of the entity, and tracking, by the device, changes to the physical characteristics over time in the eye health profile.

17. A computer program product for facilitating background monitoring of eye health of an entity, the computer program product comprising a non-transitory computer readable medium having program instructions embodied therewith, the program instructions executable by a processor to cause the processor to:

train, using training data comprising images of respective physical characteristics of entities, a neural network to determine health conditions of eyes of the entities;

monitor, in real-time using respective sensors of different devices, while an entity performs activities on the different devices, physical characteristics of the entity associated with determining possible health conditions of an eye of the entity, wherein the activities are unrelated to determining the possible health conditions of the eye, and wherein the monitoring occurs in a background of the different devices without interrupting the entity from performing the activities, and wherein the physical characteristics of the entity comprise respective viewing angles of the entity associated with sizes of images displayed on the different devices;

determine, using the neural network, a health condition of the eye of the entity from the possible health conditions based on the physical characteristics;

receive, from the entity, feedback regarding an accuracy of the determined health condition of the eye of the entity; and retrain the neural network based on the feedback.

18. The computer program product of claim 17, wherein the program instructions are further executable to cause the processor to:

present an alert based on the health condition of the eye.

19. The computer program product of claim 17, wherein the program instructions are further executable to cause the processor to:

instantiate a session with a medical professional that enables the medical professional to remotely control a device of the different devices to monitor the health condition of the eye of the entity.

20. The computer program product of claim 17, where the program instructions are further executable to cause the processor to:

generate an eye health profile of the entity, and tracks changes to the physical characteristics over time in the eye health profile.

* * * * *